(12) United States Patent
Azuma et al.

(10) Patent No.: US 8,759,489 B2
(45) Date of Patent: Jun. 24, 2014

(54) ANTIBODY IDENTIFYING AN ANTIGEN-BOUND ANTIBODY AND AN ANTIGEN-UNBOUND ANTIBODY, AND METHOD FOR PREPARING THE SAME

(75) Inventors: Takachika Azuma, Noda (JP); Hisao Takizawa, Osaka (JP)

(73) Assignees: Otsuka Pharmaceutical Co., Ltd., Tokyo (JP); Tokyo University of Science, Tokyo (JP)

( * ) Notice: Subject to any disclaimer, the term of this patent is extended or adjusted under 35 U.S.C. 154(b) by 140 days.

(21) Appl. No.: 13/217,050

(22) Filed: Aug. 24, 2011

(65) Prior Publication Data
US 2012/0157663 A1 Jun. 21, 2012

Related U.S. Application Data

(63) Continuation of application No. 12/467,853, filed on May 18, 2009, now Pat. No. 8,093,018.

(60) Provisional application No. 61/054,633, filed on May 20, 2008.

(51) Int. Cl.
| C07K 16/18 | (2006.01) |
| C07K 16/42 | (2006.01) |
| C12N 5/12 | (2006.01) |
| C12P 21/08 | (2006.01) |

(52) U.S. Cl.
USPC ............. 530/387.1; 530/388.9; 530/389.3; 435/70.21; 435/69.1

(58) Field of Classification Search
None
See application file for complete search history.

(56) References Cited

U.S. PATENT DOCUMENTS

| 5,480,974 | A |  | 1/1996 | Morgan et al. | |
| 5,977,315 | A | * | 11/1999 | Chatterjee et al. | 530/387.2 |
| 8,093,018 | B2 | * | 1/2012 | Azuma et al. | 435/70.21 |
| 2005/0031619 | A1 | * | 2/2005 | Nicodemus et al. | 424/155.1 |
| 2006/0177439 | A1 | * | 8/2006 | Koenig et al. | 424/143.1 |
| 2006/0246506 | A1 |  | 11/2006 | Pulli et al. | |
| 2007/0281318 | A1 | * | 12/2007 | Korth et al. | 435/7.1 |
| 2008/0311135 | A1 | * | 12/2008 | Zheng et al. | 424/178.1 |
| 2009/0269366 | A1 |  | 10/2009 | Cui et al. | |
| 2012/0157663 | A1 | * | 6/2012 | Azuma et al. | 530/387.2 |

FOREIGN PATENT DOCUMENTS

| CN | 1865281 A | 11/2006 |
| JP | 58-177921 A | 10/1983 |
| JP | 2004-131419 A | 4/2004 |
| WO | WO 2004/046733 A1 | 6/2004 |

OTHER PUBLICATIONS

Perosa, F. et al., "Human CD4 Internal Antigen Anti-Idiotypic Monoclonal Antibody. Immunochemical and Sequence Analysis," Clin Exp Med (2001) 2:81-89.

Extended European Search Report for EP Application No. 12177816.1 dated Nov. 6, 2012.

Cumano et al., "Structure of primary anti-(4-hydroxy-3-nitrophenyl)acetyl (NP) antibodies in normal and idiotypically suppressed C57BL/6 mice," Eur. J. Immunol., 15: 512-520 (1985).

Ju et al., "Cross-induction of Predominant $NP^b$ Idiotypic Antibodies with Derivatives of (4-hydroxy-3-nitro-phenyl) Acetyl," J. Immunology, 127(6): 2224-2228 (1981).

Oda et al., "Evidence of allosteric conformational changes in the antibody constant region upon antigen binding," International Immunology, 15(3): 417-426 (2003).

Rini et al.; "Structural Evidence for Induced Fit as a Mechanism for Antibody-Antigen Recognition," Science, 255: 959-965 (1992).

Sagawa et al., "Conformational changes in the antibody constant domains upon hapten-binding", Molecular Immunology, 42: 9-18 (2005).

International Search Report, mailed Jun. 23, 2009, for International Patent Application PCT/JP2009/059228, with translation (2 pages).

Restriction Requirement, mailed Aug. 2, 2010, for U.S. Appl. No. 12/467,853 (5 pages).

Response to Restriction Requirement, filed Sep. 2, 2010, for U.S. Appl. No. 12/467,853 (1 page).

Office Action, mailed Oct. 13, 2010, for U.S. Appl. No. 12/467,853 (12 pages).

Response to Office Action, filed Mar. 14, 2011, for U.S. Appl. No. 12/467,853 (15 pages).

Final Office Action, mailed May 24, 2011, for U.S. Appl. No. 12/467,853 (32 pages).

Mares, A. et al., "A Direct Non-Competitive Idiometric Enzyme Immunoassay for Serum Oestradiol," Journal of Immunological Methods, vol. 181, No. 1, pp. 83-90, Apr. 12, 1995.

Ullman, E.F. et al., "Anti-Immune Complex Antibodies Enhance Affinity and Specificity of Primary Antibodies," Proceedings of the National Academy of Sciences, vol. 90, pp. 1184-1189, Feb. 1, 1993.

Supplemental European Search Report for Corresponding EP Patent Application No. 09750583.8 dated Aug. 12, 2011.

Barnard et al., "Idiometric Assay: Noncompetitive Immunoassay for Small Molecules Typified by the Measurement of Estradiol in Serum," Clin. Chem., 33(11):1945-1950 (1990).

Twobin et al., "Sandwich immunoassay for the hapten angiotensin II A novel assay principle based on antibodies against immune complexes," Journal of Immunological Methods, 181:167-176 (1995).

\* cited by examiner

Primary Examiner — Phuong Huynh

(74) Attorney, Agent, or Firm — Finnegan, Henderson, Farabow, Garrett & Dunner, L.L.P.

(57) ABSTRACT

The present invention relates to an antibody that recognizes a first antibody, the antibody specifically recognizing one of a free first antibody and an antigen-binding first antibody. More specifically, the above antibody is a domino antibody that specifically recognizes and binds to an antigen-binding first antibody, or an antibody-unlocking antibody that specifically recognizes and binds to a free first antibody.

5 Claims, 24 Drawing Sheets

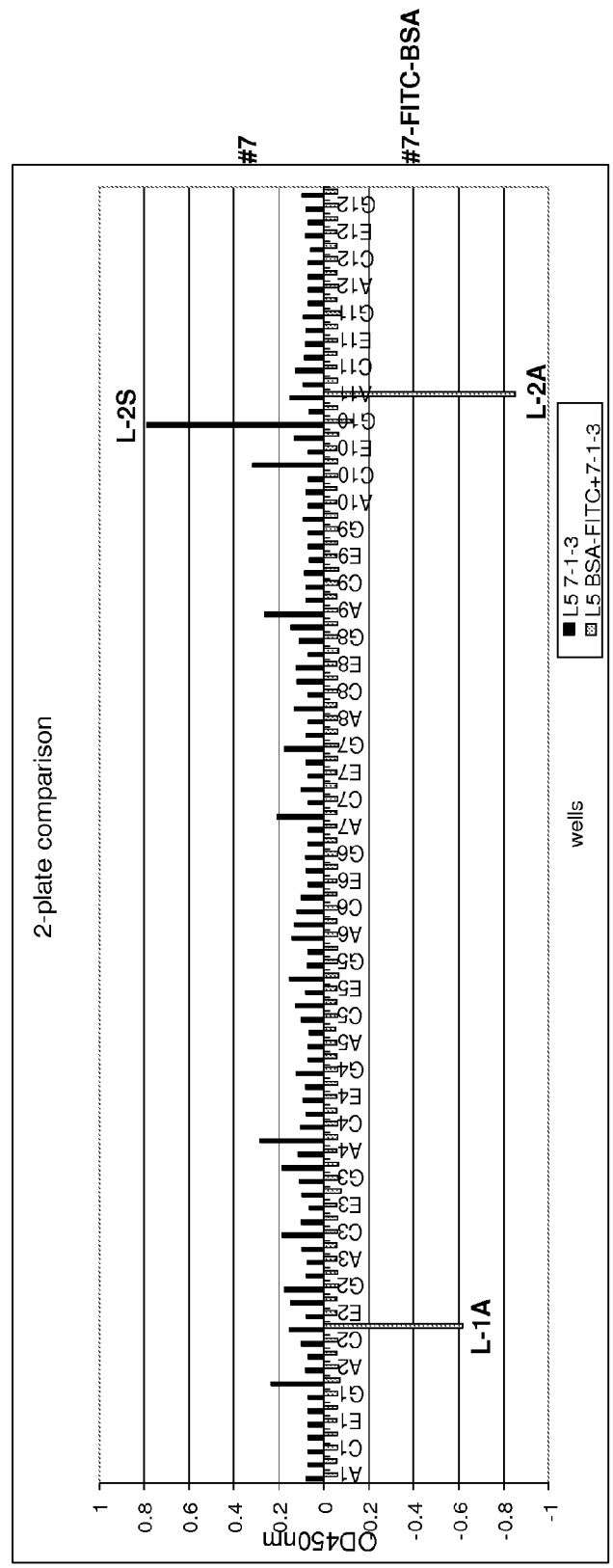

F2

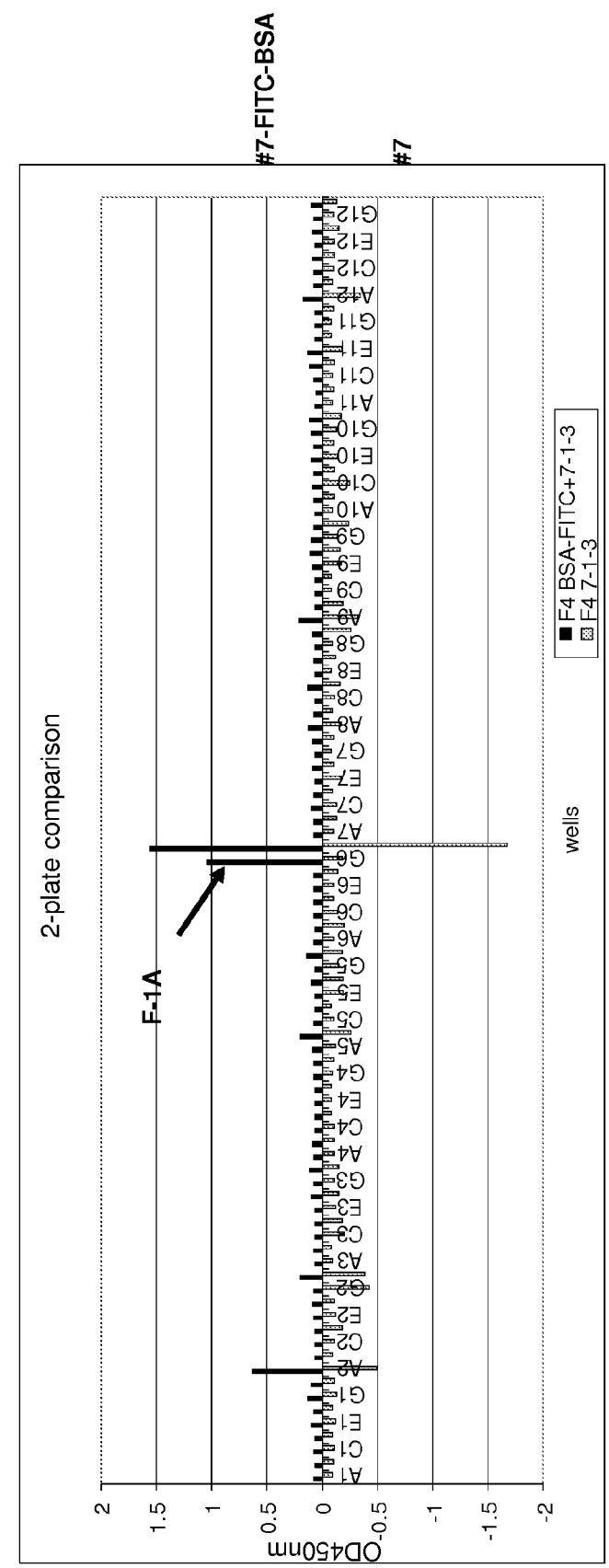

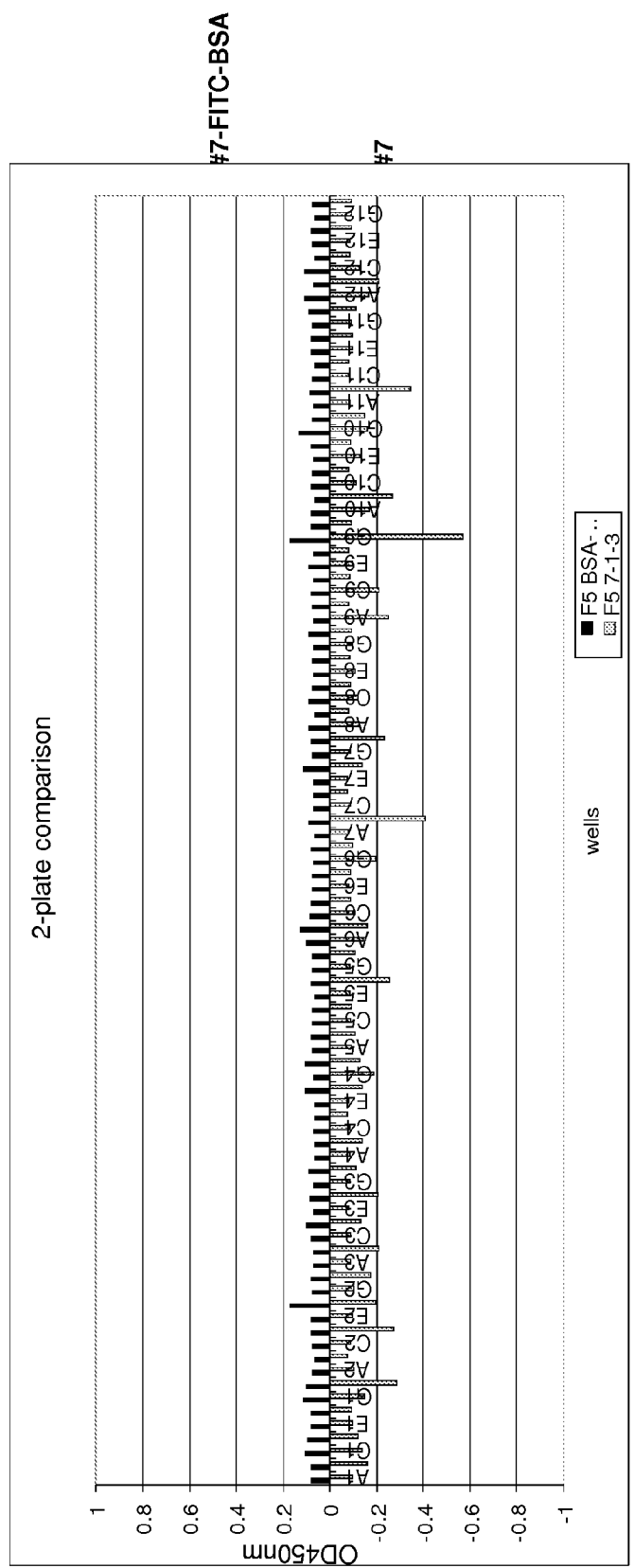

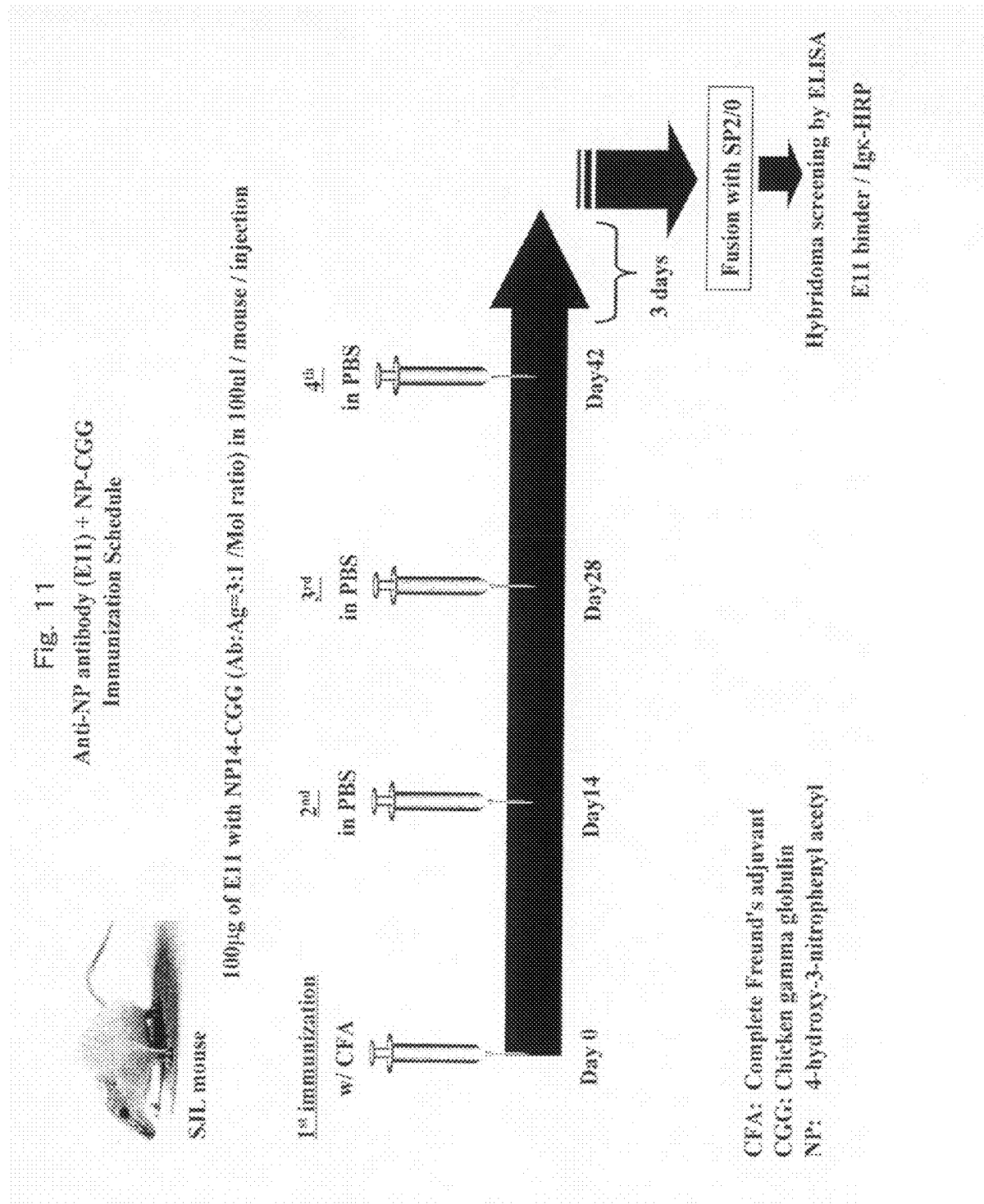

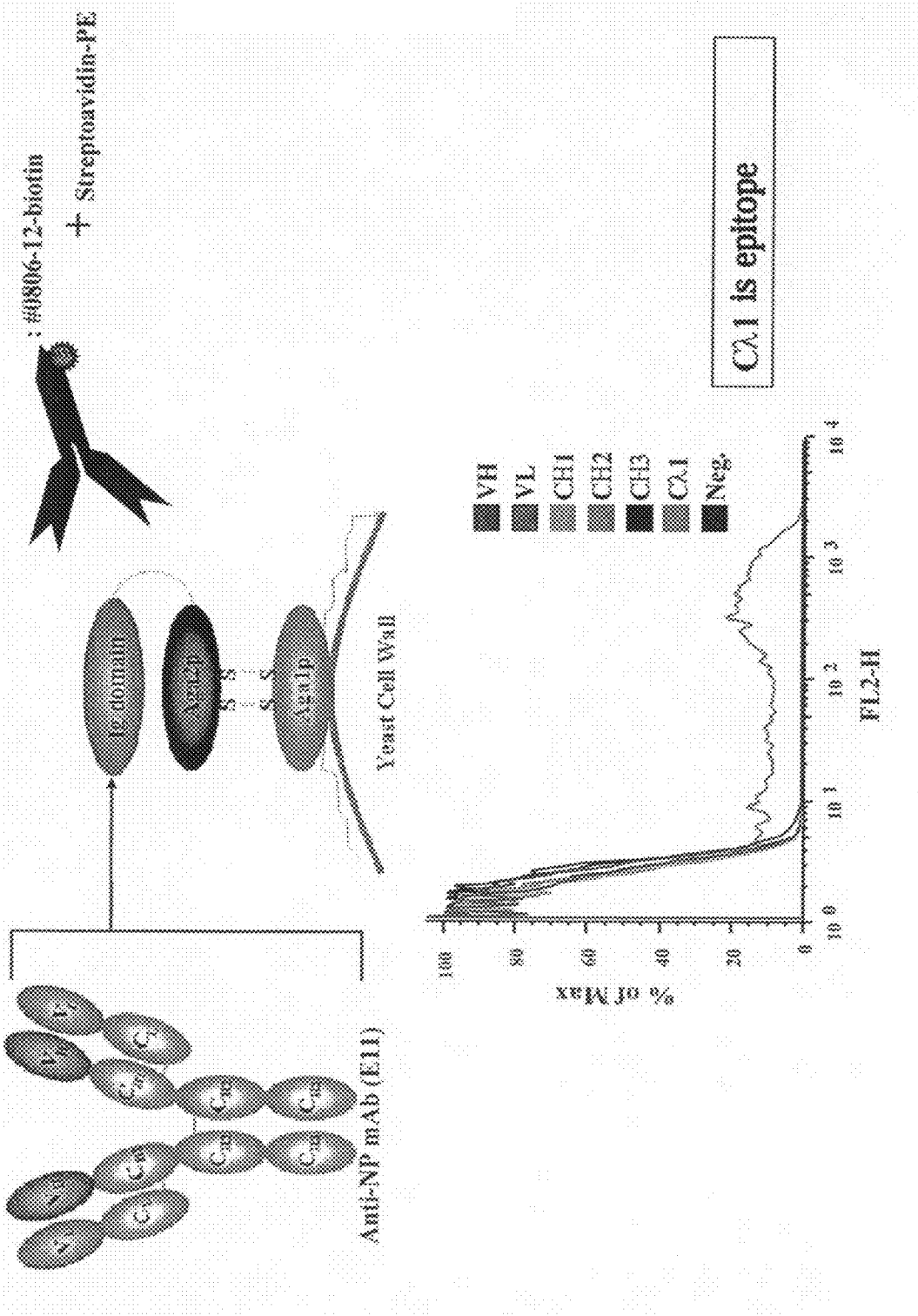

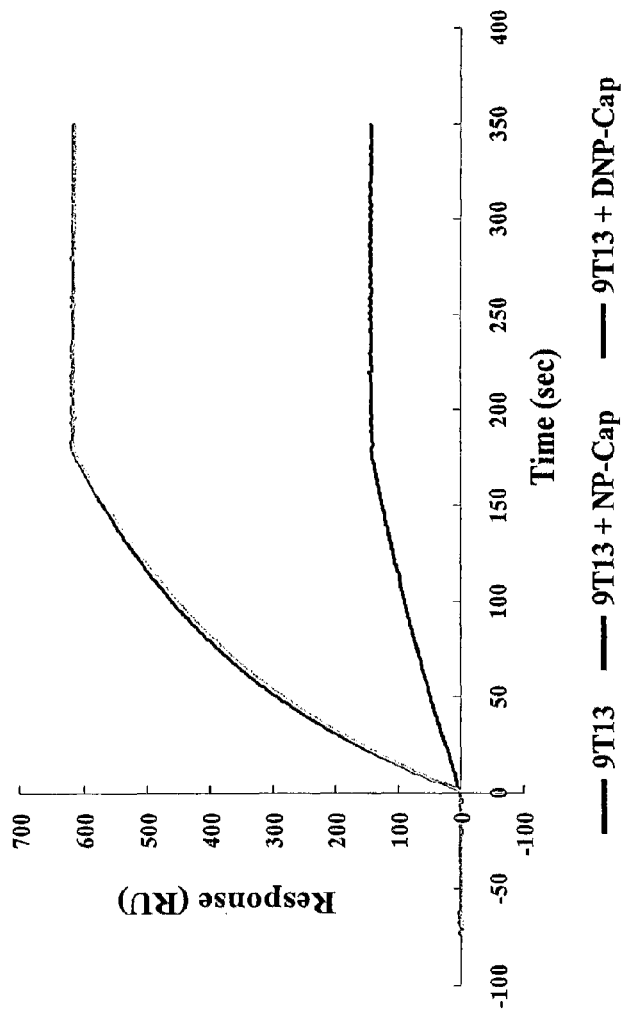

Fig. 14 Domino Antibody
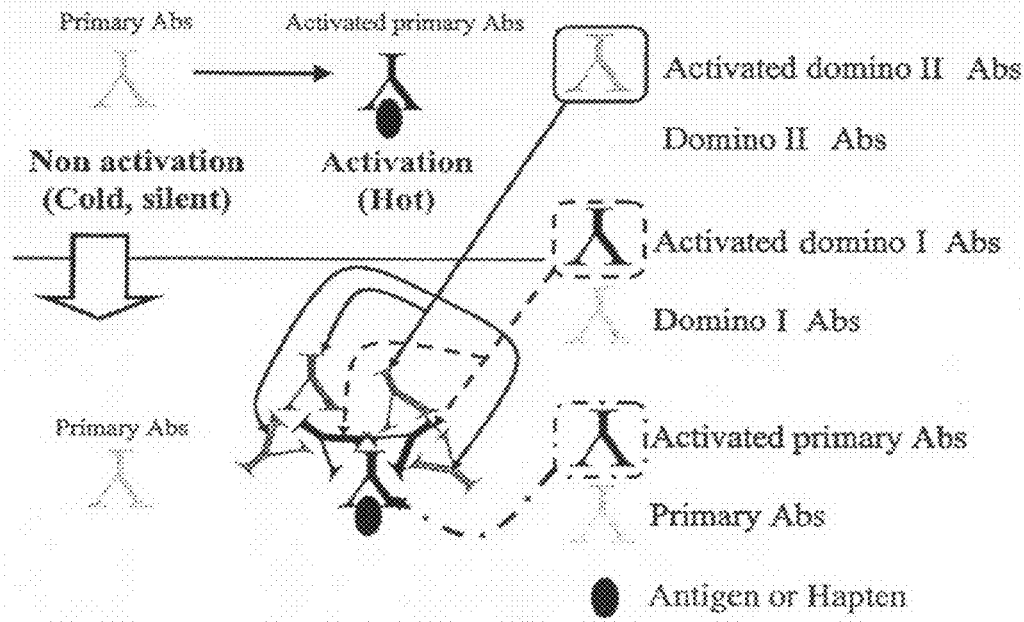
Fig. 15 Antibody unlocking antibody
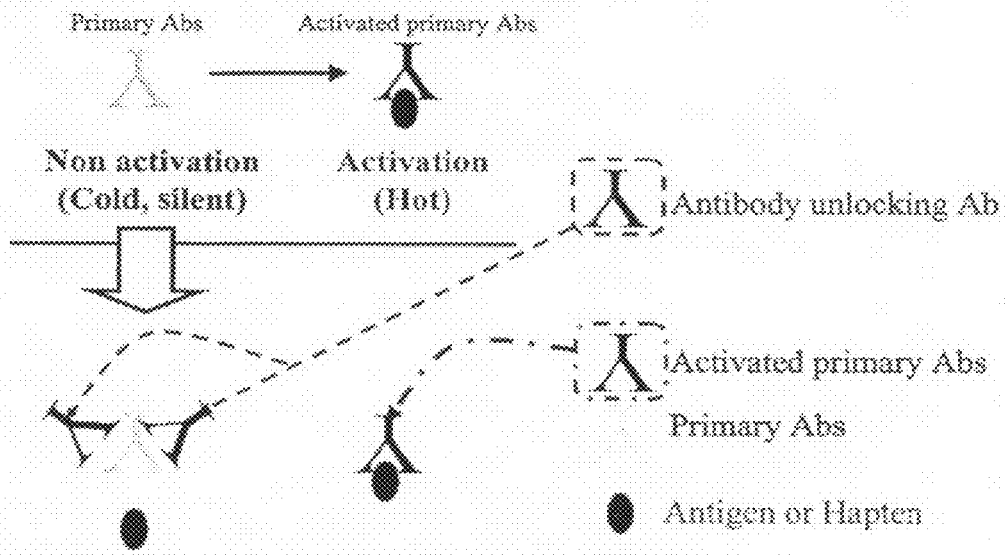

ANTIBODY IDENTIFYING AN ANTIGEN-BOUND ANTIBODY AND AN ANTIGEN-UNBOUND ANTIBODY, AND METHOD FOR PREPARING THE SAME

CROSS REFERENCE OF RELATED APPLICATION

This application is a continuation of U.S. patent application Ser. No. 12/467,853, filed May 18, 2009, now U.S. Pat. No. 8,093,018, which claims the benefit of U.S. Provisional Application No. 61/054,633 filed on May 20, 2008, both of which are incorporated herein by reference.

TECHNICAL FIELD

The present invention relates to an antibody that identifies conformational differences between an antibody bound to antigen and an antibody unbound to antigen, and a method for obtaining the same.

BACKGROUND ART

Antibodies are characterized by their specificity to identify antigens and by their binding properties. The development of monoclonal techniques has contributed to significant improvements in protein-chemical analyses of antibodies and applied technologies.

Although thermodynamic analysis and the measurement of binding reactions between antibodies and antigens can be carried out simply now, there is no detailed information on conformational changes in the antibody that accompany binding to the antigen. This is due to the difficulty of applying X-ray crystallographic analysis, which is widely used to analyze the three-dimensional protein structure, to huge proteins such as antibodies. Many structural analyses of antigen-antibody complexes are performed using Fab fragments of antibodies obtained by enzymatic digestion (Non-Patent Document 1). These analyses show that antigen binding induces conformational changes of several angstroms in amino acid residues in the antigen-binding site; however, it cannot be determined from the structural analysis of the fragments whether the changes are transmitted to a constant domain that is spatially distant from the binding site. On the other hand, antigen-antibody complexes have effector functions such as complement cascade activation, which does not exist in free antibodies. This suggests that the conformational change in the antibody caused by antigen binding is induced by the constant domain, to which the complement binds. It has, however, been interpreted that the effector functions of the complex are caused by aggregation since complement cascades are also activated by aggregates of antibodies. Meanwhile, Azuma et al. carefully analyzed the binding reaction of protein A, which is derived from *Staphylococcus aureus*, to antibodies, and found that antibodies bound to antigens and other antibodies unbound to antigens exhibited different reactivities to the protein A (Non-Patent Documents 2 and 3). However, the structural difference between free antibodies and antigen-antibody complexes, detected by protein A, was too small to be detected by ELISA etc.

Non-Patent Document 1: "Structural evidence for induced fit as a mechanism for antibody-antigen recognition", James M. Rini, Ursula Schulze-Gahmen, and Ian A. Wilson, Science, 255: 959-965 (1992)

Non-Patent Document 2: "Evidence of allosteric conformational changes in the antibody constant region upon antigen binding", Masayuki Oda, Haruo Kozono, Hisayuki Mori, and Takachika Azuma, International Immunology, 15: 417-426 (2003)

Non-Patent Document 3: "Conformational changes in the antibody constant domains upon hapten-binding", Takuma Sagawa, Masayuki Oda, Misayuki Morii, Hisao Takizawa, Haruo Kozono, and Takachika Azuma, Molecular Immunology, 42: 9-18 (2005)

DISCLOSURE OF THE INVENTION

As described above, there was no means for distinguishing free antibodies from antigen-binding antibodies in the prior art. It was therefore necessary to previously separate free antibodies and complexes in a reaction mixture, and then detect complex-forming antibodies using another antibody directed against the antibodies (anti-antibody). Furthermore, due to limited binding sites of antibody-binding proteins, such as protein A, the detection of conformational changes induced in the constant domain of antibodies was limited.

An object of the present invention is to provide an antibody that facilitates conformational changes induced in the constant domain of an antibody, and a method for producing the same.

The present invention provides the following antibody and method for producing the same.

Item 1. An antibody that recognizes a first antibody, the antibody specifically recognizing one of a free first antibody and an antigen-binding first antibody.

Item 2. The antibody according to Item 1, wherein the specific recognition antibody is a domino antibody that specifically recognizes and binds to an antigen-binding first antibody.

Item 3. The antibody according to Item 1, wherein the specific recognition antibody is an antibody-unlocking antibody that specifically recognizes and binds to a free first antibody.

Item 4. The antibody according to any one of Items 1 to 3, wherein the specific recognition antibody recognizes any one selected from the group consisting of a light chain region of a first antibody or a partial peptide of the light chain region, Fd (heavy chain variable domain and CH1 domain), and its partial peptide.

Item 5. A hybridoma producing the antibody according to any one of Items 1 to 4.

Item 6. The hybridoma according to Item 5, wherein the ATCC accession number is PTA-9167 or PTA-9168.

Item 7. A method for obtaining a domino antibody or an antibody-unlocking antibody, comprising:

carrying out immunization using gamma globulin as an antigen, and selecting a domino antibody or an antibody-unlocking antibody from monoclonal antibodies produced by the obtained hybridoma.

Item 8. The method according to Item 7, wherein the antigen is a light chain of gamma globulin, or a fragment thereof.

Item 9. A method for obtaining a domino antibody, comprising:

allowing a hapten antibody to capture a hapten or antigen, chemically fixing or bonding the hapten or antigen to the antibody to prepare an antigen-antibody complex in which the antigen does not dissociate from the antibody, and carrying out immunization using the complex.

The present invention has allowed the distinction between free antibodies and antigen-binding antibodies.

BRIEF EXPLANATION OF THE DRAWINGS

FIG. 11 shows the immunization schedule for anti-NP antibody (E11)+NP-CGG (100 μg of E11 with NP14-CGG (Ab:Ag=3:1/Mol ratio) in 100 μl/mouse/injection). In FIG. 11, the conditions are as follows:

CFA: complete Freund's adjuvant
CGG: chicken gamma globulin
NP: 4-hydroxy-3-nitrophenyl acetyl FIG. 12 shows epitope mapping of mAb #0806-12 by yeast cell surface display. Cλ1 is an epitope.

FIG. 13 shows the binding properties of anti-NP mAb to anti λ1 mAb #0806-12 in the presence or absence of NP-Ag (specimens: 9T13 mAb, 9T13 mAb+NP-Cap, or 9T13 mAb+DNP-Cap). In FIG. 13, the conditions are as follows:

Sensor chip: CM5
Flow rate: 10 ml/min
Running buffer: PBS (0.005% Tween20)
Ligand: anti-E11mAb (#0806-12), 2000 RU
Analyte conc.: 9T13 mAb (200 nM)
9T13 mAb (200 nM)+NP-Cap (1 mM)
9T13 mAb (200 nM)+DNP-Cap (1 mM)
Injection time: 3 min
Regeneration: 10 mM Gly-HCl (pH 1.6) 10 ml×4 times FIG. 14 shows the domino antibody.
FIG. 15 shows the antibody-unlocking antibody.

BEST MODE FOR CARRYING OUT THE INVENTION

Figure 1:
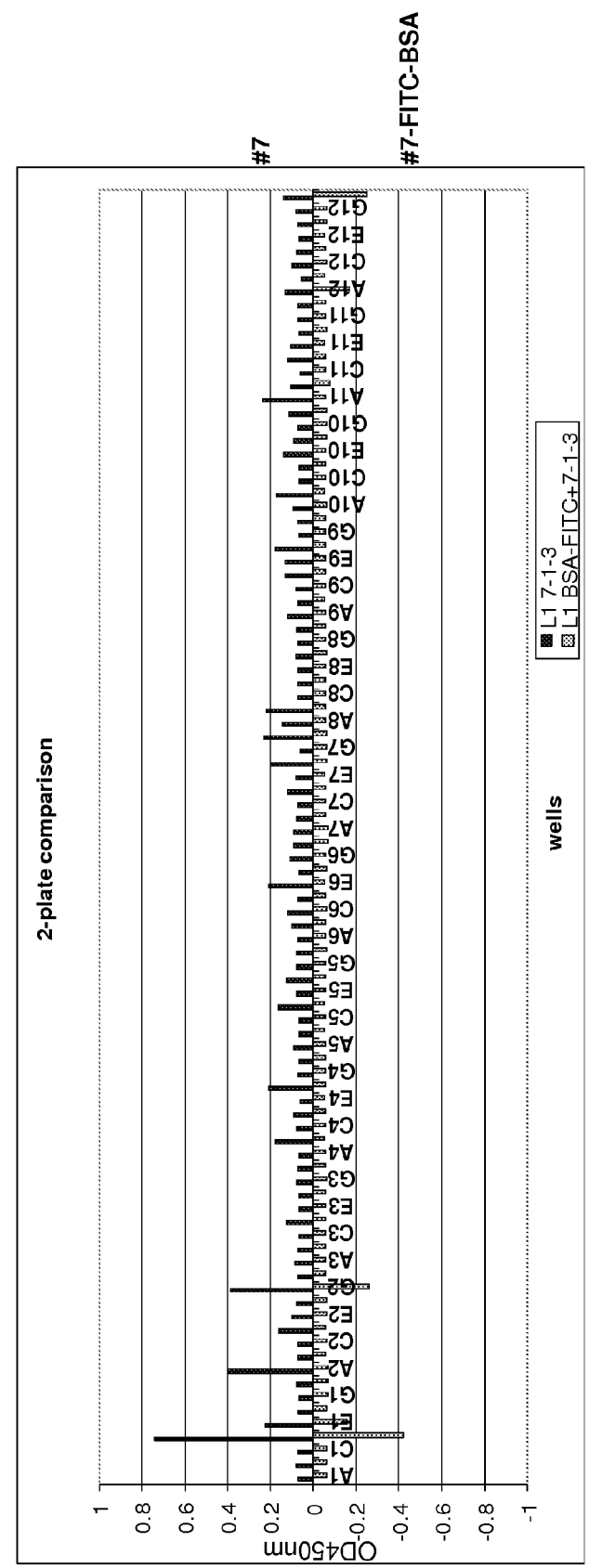
FIG. 1 shows the results obtained by the assay method for L series antibodies.
Figure 1:
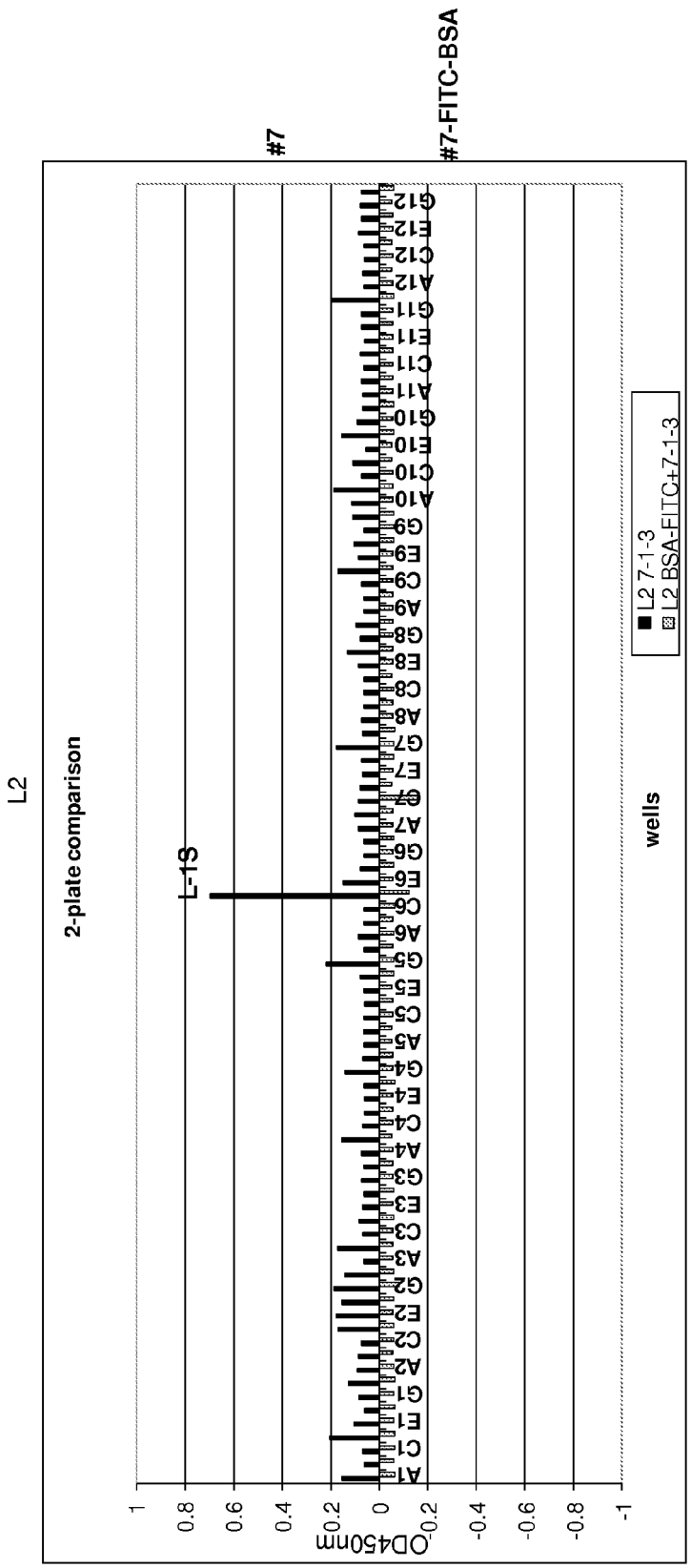

In the specification, a "first antibody" refers to an antibody recognized by another antibody (specific recognition antibody) that specifically recognizes one of the free first antibody and antigen-binding first antibody of the present invention. The first antibody recognizes an antigen, which may be an antibody or non-antibody. The "first antibody" includes both of the free first antibody and antigen-binding first antibody.

In the specification, "specifically recognizing one of a free first antibody and an antigen binding first antibody" means specifically recognizing and binding to either one of a first antibody unbound to an antigen (free first antibody) and a first antibody bound to an antigen (antigen-binding first antibody), while not binding at all or not substantially binding to the other. For example, the bond of the specific recognition antibody of the present invention to the free first antibody or antigen-binding first antibody that is not recognized by the specific recognition antibody shows an equivalent level (background level) of the bond to an antigen uninvolved in antibody recognition, such as an antigen recognized by the first antibody.

A "free first antibody" refers to a first antibody unbound to an antigen, and an "antigen-binding first antibody" refers to a first antibody bound to an antigen.

The specific recognition antibody (the antibody that specifically recognizes one of the free first antibody and the antigen-binding first antibody) of the present invention includes both a domino antibody and an antibody-unlocking antibody (AUA).

In the specification, the "domino antibody" refers to an antibody that specifically recognizes a first antibody bound to an antigen. The domino antibody recognizes antibodies such as primary antibodies and secondary antibodies. Antibodies to be recognized by the domino antibody may be complexes of antibodies (e.g., secondary antibodies and tertiary antibodies), or antibodies that bind to antigens other than antibodies (e.g., primary antibodies). When using a second domino antibody (Domino II antibody) against a first domino antibody (Domino I antibody) in combination with a third domino antibody (Domino III antibody) against the second domino antibody, the second domino antibody and the third domino antibody in turn bind to the antigen-binding first antibody. Such antibodies were thus named domino antibodies in the specification (FIG. 14).

The "antibody-unlocking antibody (AUA)" refers to an antibody that specifically recognizes a free first antibody unbound to an antigen. The antibody-unlocking antibody was so named because it can extract (unlock) an antigen or antibody from an antigen-binding antibody having a high affinity. The preferred antibody-unlocking antibody of the present invention is an antibody capable of extracting (unlocking) an antigen or antibody from an antigen-binding antibody.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments as long as they exhibit the desired biological activity.

Unless indicated otherwise, the expression "multivalent antibody" is used throughout this specification to denote an antibody comprising three or more antigen-binding sites. The multivalent antibody is preferably engineered to have the three or more antigen-binding sites and is generally not a native sequence IgM or IgA antibody.

"Antibody fragments" comprise a portion of an antibody retaining the ability to bind antigen. Examples of antibody fragments encompassed by the present definition include:
(i) the Fab fragment having VL, CL, VH and CH1 domains;
(ii) the Fab' fragment, which is a Fab fragment having one or more cysteine residues at the C-terminus of the CH1 domain;
(iii) the Fd fragment having VH and CH1 domains;
(iv) the Fd' fragment having VH and CH1 domains and one or more cysteine residues at the C-terminus of the CH1 domain;
(v) the Fv fragment having the VL and VH domains of a single arm of an antibody;
(vi) the dAb fragment (Ward et al., Nature 341: 544-546 (1989)) which consists of a VH domain;
(vii) isolated CDR regions;
(viii) F(ab')$_2$ fragments;
(ix) single chain antibody molecules (e.g., single chain Fv; scFv) (Bird et al., Science 242: 423-426 (1988); and Huston et al., PNAS (USA) 85: 5879-5883 (1988));
(x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 90: 6444-6448 (1993));

(xi) "linear antibodies" comprising a pair of tandem Fd segments (VH-CH1-VH-CH1) which, together with complementary light chain polypeptides, form a pair of antigen binding regions (Zapata et al., Protein Eng. 8(10): 1057-1062 (1995); and U.S. Pat. No. 5,641,870).

The term "monoclonal antibody" as used herein refers to an antibody obtained from a population of substantially homogeneous antibodies. That is, the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring the production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) or Marks et al., J. Mol. Biol., 222: 581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81: 6851-6855 (1984)).

"Humanized" forms of non-human (e.g., murine) antibodies are chimeric antibodies that contain minimal sequences derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as a mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature, 321: 522-525 (1986); Riechmann et al., Nature, 332: 323-329 (1988); and Presta, Curr. Op. Struct. Biol., 2: 593-596 (1992).

A "human antibody" is one which possesses an amino acid sequence which corresponds to that of an antibody produced by a human and/or has been made using any of the techniques for making human antibodies as disclosed herein. Human antibodies can be produced using various techniques known in the art. In one embodiment, the human antibody is selected from a phage library, where that phage library expresses human antibodies (Vaughan et al., Nature Biotechnology, 14: 309-314 (1996); Sheets et al., PNAS (USA), 95: 6157-6162 (1998)); Hoogenboom and Winter, J. Mol. Biol., 227: 381 (1991); and Marks et al., J. Mol. Biol., 222: 581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology, 10: 779-783 (1992); Lonberg et al., Nature, 368: 856-859 (1994); Morrison et al., Nature, 368: 812-13 (1994); Fishwild et al., Nature Biotechnology, 14: 845-51 (1996); Neuberger, Nature Biotechnology, 14: 826 (1996); and Lonberg and Huszar, Intern. Rev. Immunol., 13: 65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., J. Immunol., 147 (1): 86-95 (1991); and U.S. Pat. No. 5,750,373.

A "disorder" is any condition that would benefit from treatment with the antibody. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The term "therapeutically effective amount" refers to an amount of a drug that is effective to treat a disease or disorder in a mammal.

"Treatment" refers to both therapeutic treatment and prophylactic or preventative measures. Those in need of treatment include those already with the disorder as well as those in which the disorder is to be prevented.

The word "label" when used herein refers to a detectable compound or composition which is conjugated directly or indirectly to the polypeptide (e.g., antigen or antibody). The label may be itself be detectable (e.g., radioisotope labels or fluorescent labels) or, in the case of an enzymatic label, may catalyze chemical alteration of a substrate compound or composition which is detectable.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers.

Preparation of Monoclonal Antibody

Means for preparing and characterizing antibodies are well known in the art. A description follows as to exemplary techniques for the production of antibodies used in accordance with the present invention. The antigen to be used for the production of antibodies may be other antibodies or parts thereof, preferably light chains of the antibody or fragments thereof.

The preparation of antibodies according to the present invention is characterized by the use of light chains. Domino antibodies, which recognize only antibody complexes and do not recognize free antibodies, seem to be produced by administering antigen-antibody complexes to a host. When the present inventors actually employed this method, however, the resulting antibodies recognized both free antibodies and complex antibodies. In contrast, when light chains were used to produce antibodies, domino antibodies specifically recognizing antigen-antibody complexes, or antibody-unlocking antibodies specifically recognizing free antibodies were obtained.

Alternatively, domino antibodies can be obtained by chemically fixing or binding haptens or antigens to hapten antibodies after haptens or antigens are captured by hapten antibodies, producing antigen-antibody complexes in which the antigens do not dissociated from the antibodies, followed by immunization against the complexes. Examples of haptens include steroid hormones, such as testosterone, estradiol, estriol, and cortisol; compounds having mononitrophenyl, dinitrophenyl, trinitrophenyl, fluoresceine and other groups (e.g., 2,4-dinitrophenol (DNP)); and low-molecular substances represented by digoxin and low-molecular drugs, which can be administered to mammals such as mice, thereby inducing antibodies against the substances. Hapten antibodies specifically recognize these haptens. Chemical fixation or binding of haptens or antigens to antibodies can be achieved using cross linking agents, e.g., glutaraldehyde, formaldehyde, paraformaldehyde, and other dialdehydes, and tolylene-2,4-diisocyanate, and other diisocyanates.

The domino antibody and antibody-unlocking antibody of the present invention may be made using light chains or fragments thereof, and using the hybridoma method first described by Kohler et al., Nature, 256: 495 (1975), or may be made using recombinant DNA methods (U.S. Pat. No. 4,816,567).

In a preferred embodiment of the present invention, domino antibodies and antibody unlocking antibodies can be produced by the hybridoma method in which the light chains of antibodies to be recognized by the domino antibodies or antibody-unlocking antibodies are obtained and administered to a host (mouse, rat, rabbit, hamster, macaque monkey, etc.) as sources of immunization. For example, a host is immunized as hereinabove described to elicit lymphocytes that produce or are capable of producing antibodies that will specifically bind to the light chain or its fragment used for immunization. Alternatively, lymphocytes may be immunized in vitro. Lymphocytes are then fused with myeloma cells using a suitable fusing agent, such as polyethylene glycol, to form a hybridoma cell (Goding, Monoclonal Antibodies: Principles and Practice, pp. 59-103 (Academic Press, 1986)).

Although the feature of this monoclonal antibody acquisition is the use of light chains as antigens, as described above, target antibody producing hybridomas can also be obtained by using, as antigens, H chains and H chain fragments including the variable region and CH1 region of the H chain.

More specifically, an antibody captures an antigen at two Fab regions, each of which is composed of a light chain (VL+CL) and a heavy chain Fd (heavy chain variable region (VH)+CH1 region). The light chain (VL+CL) and Fd (VH+CH1) in Fab are a pair of functionally symmetric proteins. In VL of this pair of proteins, three divided regions (hypervariable regions) exist, and similarly, three divided regions (hypervariable regions) exist in VH at locations corresponding to those in VL. Antigens are captured by these portions. The fact that domino antibodies and antibody unlocking antibodies are obtained by immunizing L chains means that when an antibody captures an antigen, a conformational change occurs in the L chain of the Fab portion of the antibody. Therefore, in other words, antibodies capable of distinguishing conformational changes in L chains are supposed to be domino antibodies and antibody unlocking antibodies. No one believed that the antigen ligation reaction of antibodies induces conformational changes in L chains, and that antibodies capable of recognizing portions where such conformational changes occur can be obtained. The present invention has been accomplished based on these findings.

As described above, when focusing on Fab of an antibody, L and H chains are a pair of functionally symmetric proteins. Since the conformational change was expected in the L chain through acquisition of the domino antibody and antibody-unlocking antibody this time, similar conformational changes presumably occur due to antigen capture in the Fd of the heavy chain, which is the corresponding protein in the above pair. In other words, domino antibodies and antibody unlocking antibodies are presumably obtained by immunization with a heavy chain Fd portion or a fragment thereof, and performing a similar screening process.

However, immunization with light chains is superior in the following respects:

(i) Fd is supposed to be purified after the purification of Fab and F(ab')$_2$. In this respect, it is simpler to purify light chains and the yield is more advantageous; and (ii) light chains are easier to handle in terms of physicochemical properties. The H chain is a hydrophobic protein, and is easily precipitated during purification.

However, the above-mentioned defects of the H chain can be avoided by, for example, 1) immunizing with a chemically synthesized partial peptide of Fd, 2) obtaining a recombinant protein consisting only of Fd in *E. coli* or yeast, and 3) conducting immunization using KO mice lacking specific Fd portions.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen (free antibody or antigen-binding antibody). Preferably, the binding specificity of monoclonal antibodies (domino antibodies or antibody-unlocking antibodies) produced by hybridoma cells is determined by immunoprecipitation or by an in vitro binding assay, such as radioimmunoassay (RIA) or enzyme-linked immunoabsorbent assay (ELISA).

After hybridoma cells are identified that produce, as the domino antibodies or antibody-unlocking antibodies, antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors that are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described in McCafferty et al., Nature, 348: 552-554 (1990). Clackson et al., Nature, 352: 624-628 (1991), and Marks et al., J. Mol. Biol., 222: 581-597 (1991) describe the isolation of murine and human antibodies, respectively, using phage libraries. Other documents describe the production of high affinity (nM range) human antibodies by chain shuffling (Marks et al., Bio/Technology, 10: 779-783 (1992)), as well as combinatorial infection and in vivo recombination as a strategy for constructing very large phage libraries (Waterhouse et al., Nuc. Acids. Res., 21: 2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81: 6851 (1984)), or by covalently joining to the immunoglobulin coding sequence all or part of the coding sequence for a non-immunoglobulin polypeptide.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321: 522-525 (1986); Riechmann et al., Nature, 332: 323-327 (1988); and Verhoeyen et al., Science, 239: 1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151: 2296 (1993); and Chothia et al., J. Mol. Biol., 196: 901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89: 4285 (1992); and Presta et al., J. Immunol., 151: 2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255-258 (1993); Bruggermann et al., Year in Immuno., 7: 33 (1993); and Duchosal et al., Nature, 355: 258 (1992). Human antibodies can also be derived from phage-display libraries (Hoogenboom et al., J. Mol. Biol., 227: 381

(1991); Marks et al., J. Mol. Biol., 222: 581-597 (1991); Vaughan et al., Nature Biotech, 14: 309 (1996)).

Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods, 24: 107-117 (1992) and Brennan et al., Science, 229: 81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology, 10: 163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

It may be desirable to modify the antibody of the invention with respect to effector function so as to enhance the effectiveness of the antibody. For example, cysteine residue(s) may be introduced in the Fc region, thereby allowing inter-chain disulfide bond formation in this region. The homodimeric antibody thus generated may have improved internalization capability and/or increased complement-mediated cell killing and antibody-dependent cellular cytotoxicity (ADCC). See Caron et al., J. Exp. Med., 176: 1191-1195 (1992) and Shopes, B. J. Immunol., 148: 2918-2922 (1992). Homodimeric antibodies with enhanced anti-tumor activity may also be prepared using heterobifunctional cross-linkers as described in Wolff et al., Cancer Research, 53: 2560-2565 (1993). Alternatively, an antibody can be engineered which has dual Fc regions and may thereby have enhanced complement lysis and ADCC capabilities. See Stevenson et al., Anti-Cancer Drug Design, 3: 219-230 (1989).

The antibody disclosed herein may also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide interchange reaction. A chemotherapeutic agent (such as Doxorubicin) is optionally contained within the liposome. See Gabizon et al., J. National Cancer Inst., 81 (19) 1484 (1989).

Covalent modifications of the antibody are included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Covalent modifications involve chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, CRC Crit. Rev. Biochem., pp. 259-306 (1981).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin et al., Arch. Biochem. Biopliys., 259: 52 (1987) and by Edge et al., Anal. Biochem., 118: 131 (1981). Enzymatic cleavage of carbohydrate moieties on antibodies can be achieved by the use of a variety of endo- and exo-glycosidases as described by Thotakura et al., Meth. Enzymol., 138: 350 (1987).

Another type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

The antibody of the invention can be produced recombinantly.

For recombinant production of an antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Therapeutic formulations of the antibodies used in accordance with the present invention are prepared for storage by mixing an antibody having the desired degree of purity with optional pharmaceutically acceptable carriers, excipients or stabilizers (Remington's Pharmaceutical Sciences, 16th edition, Osol, A. Ed. [1980]), in the form of lyophilized formulations or aqueous solutions. Typically, an appropriate amount of a pharmaceutically acceptable salt is used in a carrier so as to make the formulation isotonic. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Preferred lyophilized antibody formulations are described in WO 97/04801, expressly incorporated herein by reference.

The formulation herein may also contain more than one active compound as necessary for the particular indication being treated, preferably those with complementary activities that do not adversely affect each other. The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, whose matrices are in the form of shaped articles, e.g., films or microcapsules. Examples of sustained-release matrices include polyesters, hydrogels (for example, poly(2-hydroxyethyl-methacrylate) or poly(vinyl alcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be an intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage and Administration

The antibodies of the invention are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

Depending on the type and severity of the disease, about 1 μg/kg to 50 mg/kg (e.g., 0.1-20 mg/kg) of antibody is an initial candidate dosage for administration to the patient, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. In a preferred aspect, the antibody of the invention is administered every two to three weeks, at a dose ranged from about 5 mg/kg to about 15 mg/kg. The progress of the therapy of the invention is easily monitored by conventional techniques and assays.

The antibody of the invention may be administered alone or in combination with other antibody drugs.

The antibody of the invention is useful in immunoassay such as ELISA, since it recognizes the free first antibody in distinction from the antigen-binding first antibody.

Deposit of Materials

The following three hybridoma cell lines have been deposited under the provisions of the Budapest Treaty with the American Type Culture Collection (ATCC), Manassas, Va., USA:

(1) Identification Reference by Depositor: Hybridoma Cell Line F-1A
  ATCC Patent Deposit Designation: PTA-9167
  Date of Receipt of Cultures by the ATCC: Apr. 23, 2008;
(2) Identification Reference by Depositor: Hybridoma Cell Line L-6A
  ATCC Patent Deposit Designation: PTA-9168
  Date of Receipt of Cultures by the ATCC: Apr. 23, 2008; and
(3) Identification Reference by Depositor: Hybridoma Cell Line 0806-12
  ATCC Patent Deposit Designation: PTA-9967
  Date of Receipt of Cultures by the ATCC: Apr. 16, 2009.

Although the present invention is based on antibodies, the target of the invention may be nucleic acids (aptamers) or peptides, which are alternatives to antibodies. In other words, an aptamer and peptide that recognize an antibody that has recognized an antigen are synonymous with an antibody, aptamer and peptide that recognize an aptamer that has recognized an antigen. The target molecule of an aptamer can be obtained through the SELEX process, and that of a peptide can be obtained from phage libraries.

EXAMPLES

The present invention is described in detail below with reference to examples, which are merely intended to illustrate and not to limit the scope of the invention.

Example 1

Production of Domino Antibody and
Antibody-Unlocking Antibody (AUA)

Preparation of Rat Monoclonal Antibody that is Used as Antigen

Anti-FITC rat monoclonal antibody #55 (IgG2aκ) was established by a standard method. Separately, anti-FITC rat monoclonal antibody #7 (IgG2aκ) was established by a standard method. More specifically, chicken gamma globulin (CGG) (Rockland Immunochemicals, Inc., PA, USA) and bovine serum albumin (BSA) (Sigma, Mo., USA) were labeled with FITC using an FITC labeling kit (Dojindo, Kumamoto, Japan). The FITC-labeled CGG (80 μg/100 μl in PBS) was mixed with the same amount of adjuvant Titer Max Gold (CytRx Corp., GA, USA) to form an emulsion. The emulsion was intraperitoneally administered to a 7-week-old female Fischer rat for immunization three times every two weeks. After another two weeks, the same amount of FITC labeled CGG (80 μg/100 μl in PBS) was intraperitoneally administered without an adjuvant. Three days later, the spleen was extracted from the rat, and splenic cells were isolated and fused with mouse myeloma cells (P3U1) using polyethylene glycol by a standard method. Using a HAT medium as a cell selective medium, the fused cells were plated on ten 96-well plates. Fourteen days later, the culture supernatant was collected from each well, and myeloma producing anti-FITC antibodies were selected using an ELISA plate that was coated with the FITC-labeled BSA and blocked with BSA. Repeating the above-described fusion process twice, hybridomas each producing anti-FITC rat monoclonal antibody #55 (IgG2aκ) and anti-FITC rat monoclonal antibody #7 (IgG2aκ) were established by each process, respectively. Each hybridoma was cultured in large quantities, and rat monoclonal antibodies were purified from the culture supernatant using a HiTrap Protein G HP (GE Healthcare, N.J., USA) column.

Purification of the Light Chain

Light chains were purified from the anti-FITC rat monoclonal antibody #55 obtained by the above procedure. The process of separation and purification of the light chains was based on Azuma, T. et al., PNAS (1981) 78, pp 569-573. More specifically, the purified antibody #55 was dissolved in dithiothreitol and Tris-HCl (pH 8.2) at final concentrations of 0.01 M and 0.2 M, respectively. The solution was warmed to 37° C. for 30 minutes. After the reaction, the solution was cooled to room temperature (allowed to stand for about 10 minutes), and iodoacetoamide was added to give a final concentration of 0.3 M. After allowing the solution to stand for 30 minutes, an alkylation reaction was performed. The heavy and light chains were separated using HPLC. After the alkylation reaction, the alkylated antibody #55 was applied to a column equilibrated with PBS (pH 7.2) in which 5 M Guanidine-HCl was dissolved, and the light chain fraction was obtained. The fraction containing heavy chains was applied to HPLC again to obtain the light chain fraction. After the light chain fraction was dialyzed against PBS, the fraction was divided into small portions and cryopreserved.

Immunization with Light Chain and Preparation of Hybridoma

The light chains of antibody #55 (30 μg/100 μl in PBS) were mixed with the same amount of adjuvant Titer Max Gold (CytRx Corp., GA, USA) to form an emulsion. The emulsion was intraperitoneally administered to a 7-week-old female Balb/c mouse for immunization three times every two weeks. After another two weeks, the same amount of the light chains of antibody #55 (80 μg/100 μl in PBS) was intraperitoneally administered without an adjuvant. Three days later, the spleen was extracted from the mouse, and splenic cells were isolated and fused with mouse myeloma cells (P3U1) using polyethylene glycol by a standard method. Using a HAT medium as a cell selective medium, the fused cells were plated on ten 96-well plates (L series).

Antibody Assay Method

Fourteen days later, the culture supernatant was collected from each well, and an assay was performed using the following three ELISA plates: (i) a plate coated with the FITC-labeled BSA and blocked with BSA; (ii) a plate coated with the FITC-labeled BSA and blocked with BSA, the plate then being reacted with 100 μl/well of antibody #7 (1 μg/ml in PBS) at 4° C. overnight, followed by washing; and (iii) a plate coated with 100 μl/well of antibody #7 (1 μg/ml in PBS) and blocked with BSA. More specifically, 100 μl of the culture supernatant of each hybridoma was applied to the three plates, and allowed to stand at room temperature for two hours. After washing, the plates were reacted with HRP-labeled anti-mouse IgG (non-cross reacting rat IgG) (Jackson Laboratories) at room temperature for an hour. The plates were then washed, and 100 μl of a coloring solution, i.e., a TMB substrate solution (KPL, MD, USA) was added thereto. After a 10-minute reaction, 50 μl of 2N sulfuric acid was added to stop the coloring reaction, and a wavelength of 450 nm was read using a plate reader.

Evaluation of Results

Comparing the OD of plates (ii) and (iii), the hybridomas that produced antibodies strongly responding to either of the plates were determined to be the target antibody-producing hybridomas. An assay using plate (i) was suitably performed to confirm that no reaction was observed against BSA or BSA-FITC.

Alternative Method

Theoretically, when antibody A recognizes protein B as an antigen, their antigen-antibody complex (A-B) can be administered to an animal such as a mouse to obtain antibodies capable of recognizing conformational changes in antibody A, which are induced upon recognition of antigen B. The complex may be immobilized using a crosslinking agent so that the conformational change in antibody A is sustained in vivo for a long period of time.

However, various antibodies appearing in the serum of an immune animal include those responding to antibody A regardless of conformational changes in the antibody, those responding to antigen B, those recognizing conjugates of A-B, and the like. Antibodies that recognize conformational changes in antibody A accompanying the binding of A to B, like the target antibodies, seem very unlikely to appear.

For this reason, a method for effectively obtaining the present antibody was established by further simplifying immunogens and immunization procedures, A fluorescent substance FITC (fluorescein isothiocyanate) responds to the amino groups of a protein that is charged in a slightly acidic solution to form a thiourea bond, thereby easily labeling the protein. Further, FITC is known as a hapten that is capable of obtaining antibodies with high affinity. Taking advantage of this property, first, the present inventors obtained two types of anti-FITC antibodies with high affinity (antibodies #55 (IgG2aκ) and #7 (IgG2aκ), described above).

Preparation of FITC-Capturing Antibody #55

1) FITC dissolved in DMSO was added to the purified antibody #55 dissolved in PBS (pH 6.8) so that the molar ratio was about 1:5. The mixture was readily applied to a PD-10 column for demineralization (GE Healthcare Bio-Science Corp., NJ, USA) which had previously been equilibrated with PBS (pH 6.8), and the high-molecular weight fraction was isolated. Immediately, 0.5 volume of 1 M sodium carbonate buffer (pH 8.3) was added so as to make the mixture slightly alkaline. The mixture was allowed to stand under light shielding conditions at room temperature for one hour. The wavelengths of 280 nm and 495 nm were measured by a spectrophotometer, and the number of bonds of FITC molecules to one antibody molecule was calculated by a formula, confirming that the ratio of antibody molecule to FITC was almost 1:2. It was estimated from this process that FITC bound to high-affinity antibody #55 against FITC forms a covalent bond with charged amino acids in the vicinity of the antibody-binding site, allowing FITC to be continuously and stably bound to the antibody.

Immunization with FITC-Capturing Antibody #55 and Preparation of Hybridoma

FITC-capturing antibody #55 (30 µg/100 µl in PBS) was mixed with the same amount of adjuvant Titer Max Gold (CytRx Corp., GA, USA) to form an emulsion. The emulsion was intraperitoneally administered to a 7-week-old female Balb/c mouse for immunization three times every two weeks. Another two weeks later, the same amount of FITC-capturing antibody #55 (80 µg/100 µl in PBS) was intraperitoneally administered without an adjuvant. Three days later, the spleen was extracted from the mouse, and splenic cells were isolated and fused with mouse myeloma cells (P3U1) using polyethylene glycol by a standard method. Using a HAT medium as a cell selective medium, the fused cells were plated on ten 96-well plates (F series).

Antibody Assay Method

Fourteen days later, the culture supernatant was extracted from each well, and an assay was performed using the following three ELISA plates: (i) a plate coated with the FITC-labeled BSA and blocked with BSA; (ii) a plate coated with the FITC-labeled BSA and blocked with BSA, the plate being reacted with 100 µl/well of antibody #7 (1 µg/ml in PBS) at 4° C. overnight, followed by washing; and (iii) a plate coated with 100 µl/well of antibody #7 (1 µg/ml in PBS) and blocked with BSA. More specifically, 100 µl of the culture supernatant of each hybridoma was applied to the three plates, and allowed to stand at room temperature for two hours. After washing, the plates were reacted with HRP-labeled anti-mouse IgG (non-cross reacting rat IgG) (Jackson Laboratories) at room temperature for an hour. The plates were then washed, and 100 µl of a coloring solution, i.e., a TMB substrate solution (KPL, MD, USA) was added thereto. After a 10-minute reaction, 50 µl of 2N sulfuric acid was added to stop the coloring reaction, and a wavelength of 450 nm was read using a plate reader.

Evaluation of Results

Comparing the OD of plates (ii) and (iii), the hybridomas that produced antibodies strongly responding to either of the plates were determined to be the target antibody-producing hybridomas. An assay using plate (i) was suitably performed to confirm that no reaction was observed against BSA or BSA-FITC.

Figure 2:
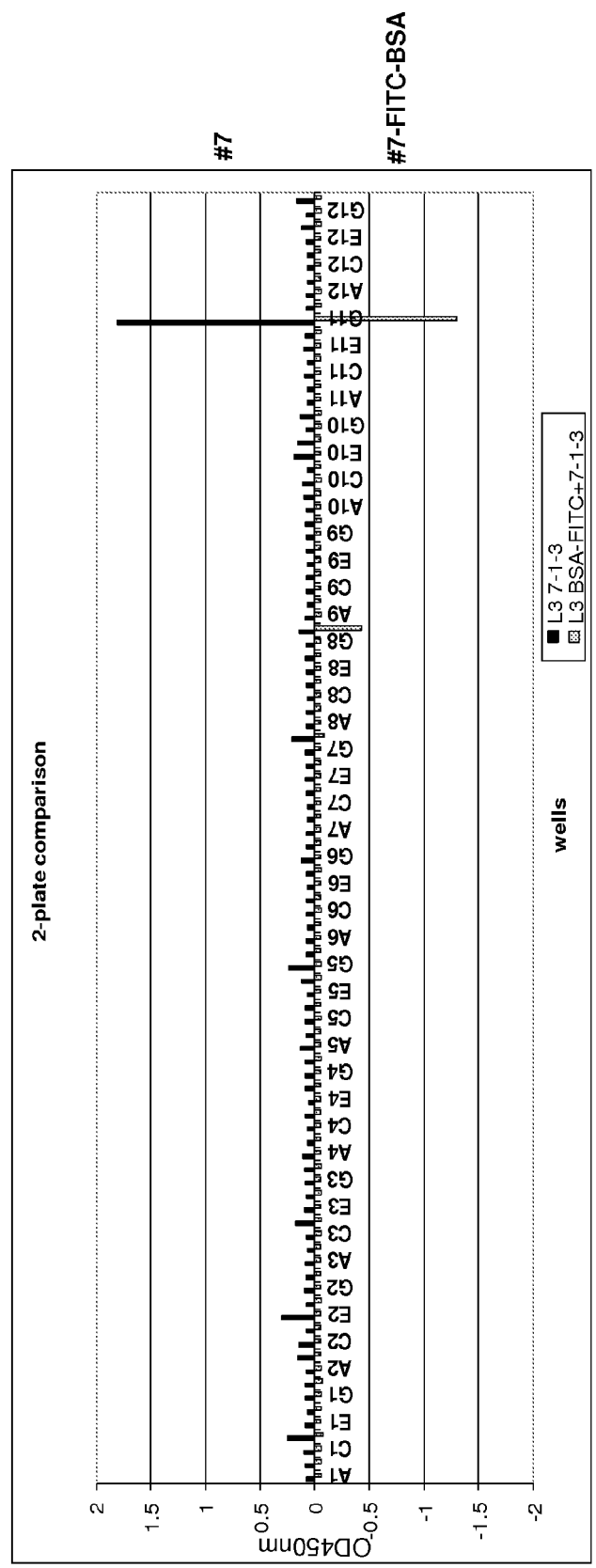
FIG. 2 shows the results obtained by the assay method for L series antibodies.
Figure 2:
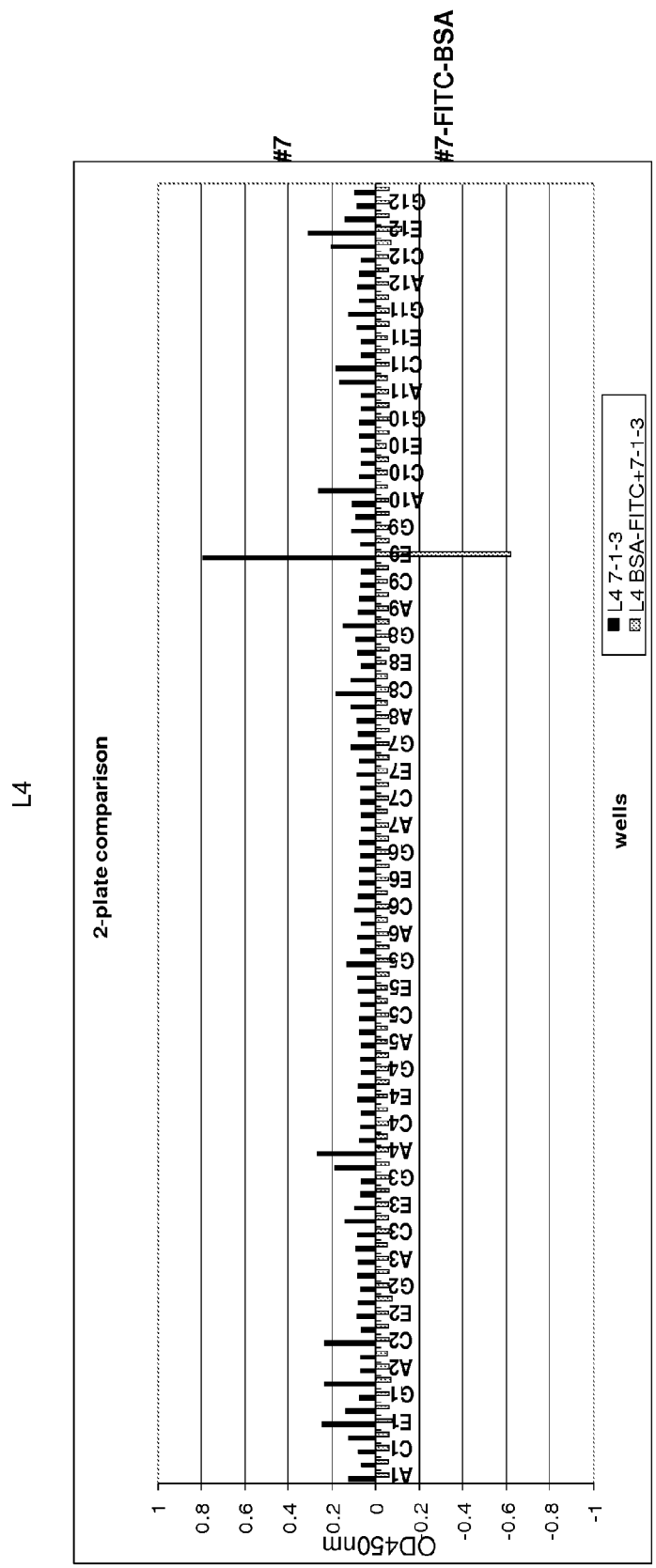
Figure 3:
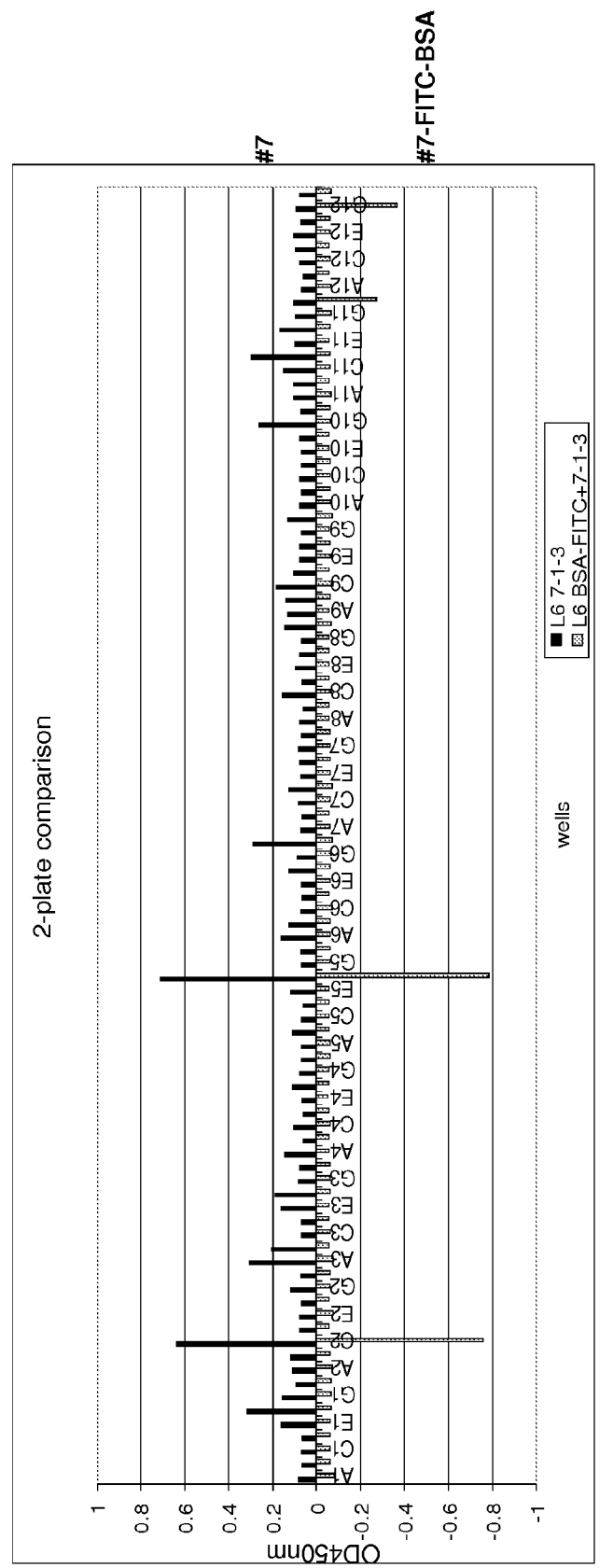
FIG. 3 shows the results obtained by the assay method for L series antibodies.
Figure 4:
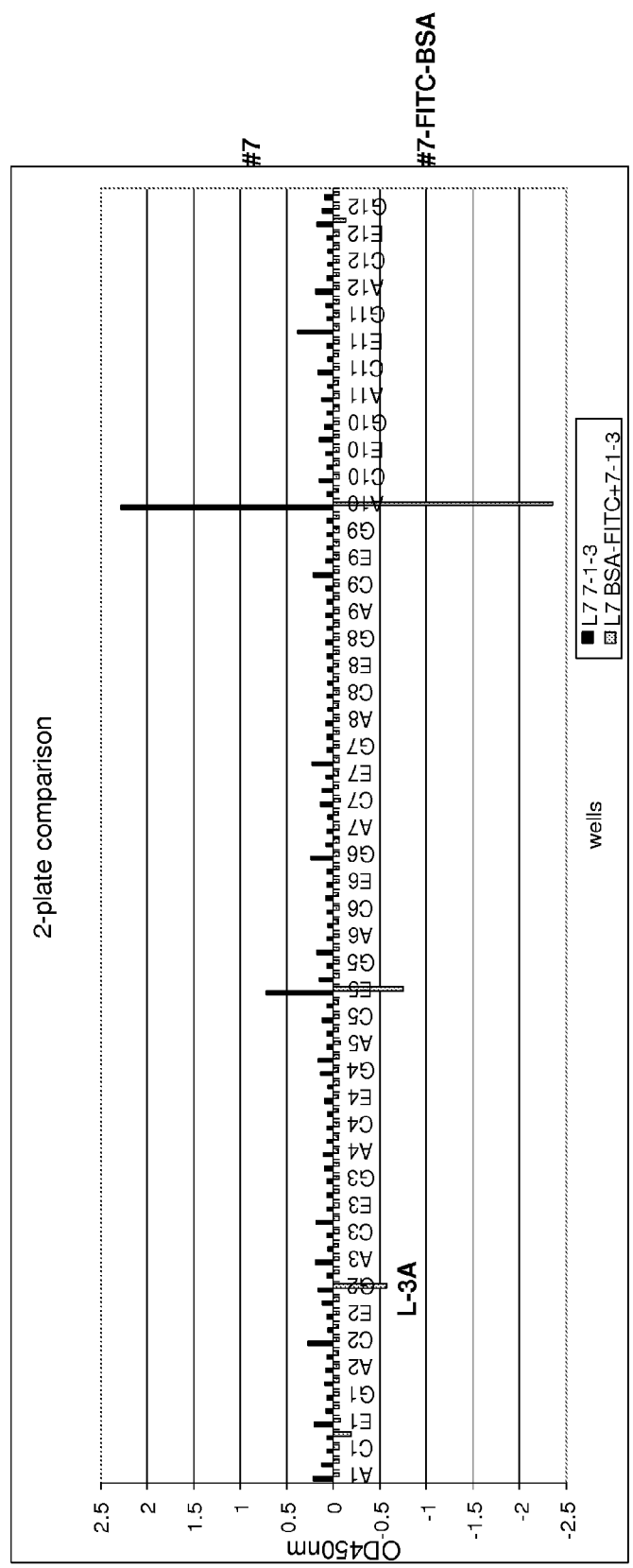
FIG. 4 shows the results obtained by the assay method for L series antibodies.
Figure 4:
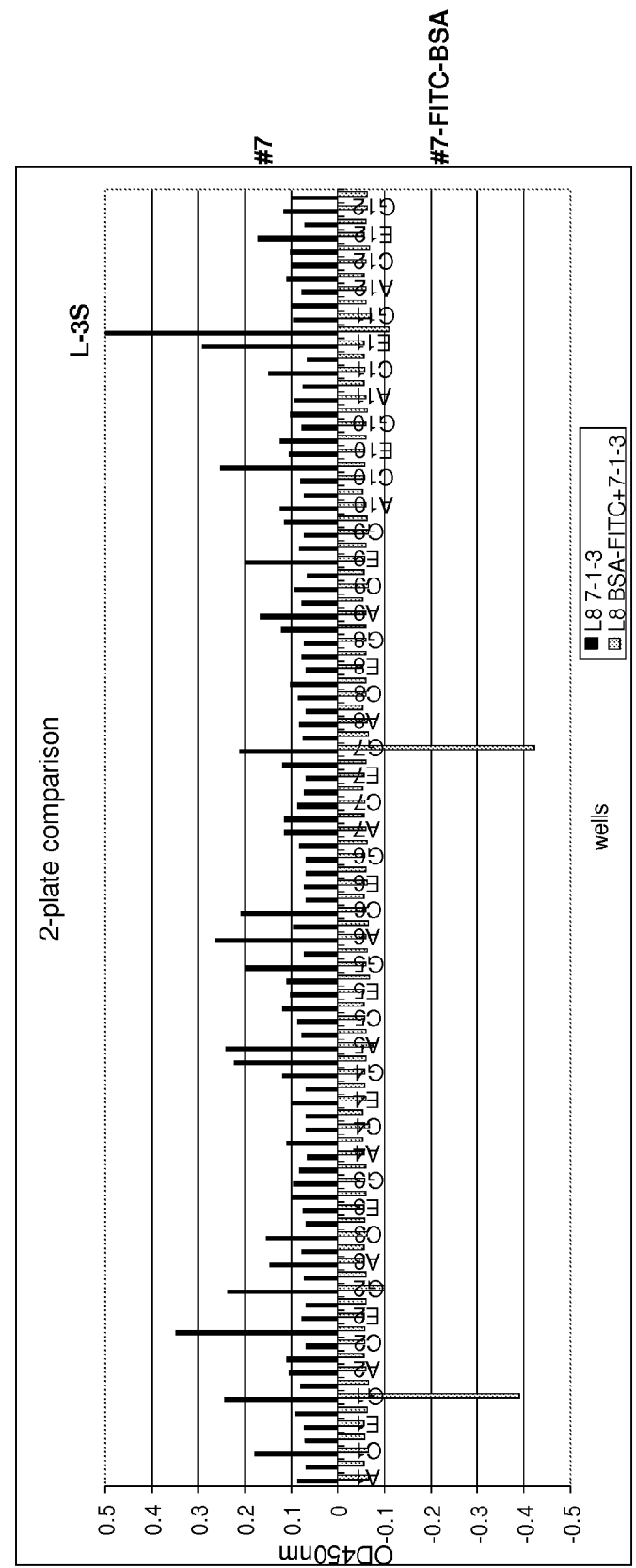
Figure 5:
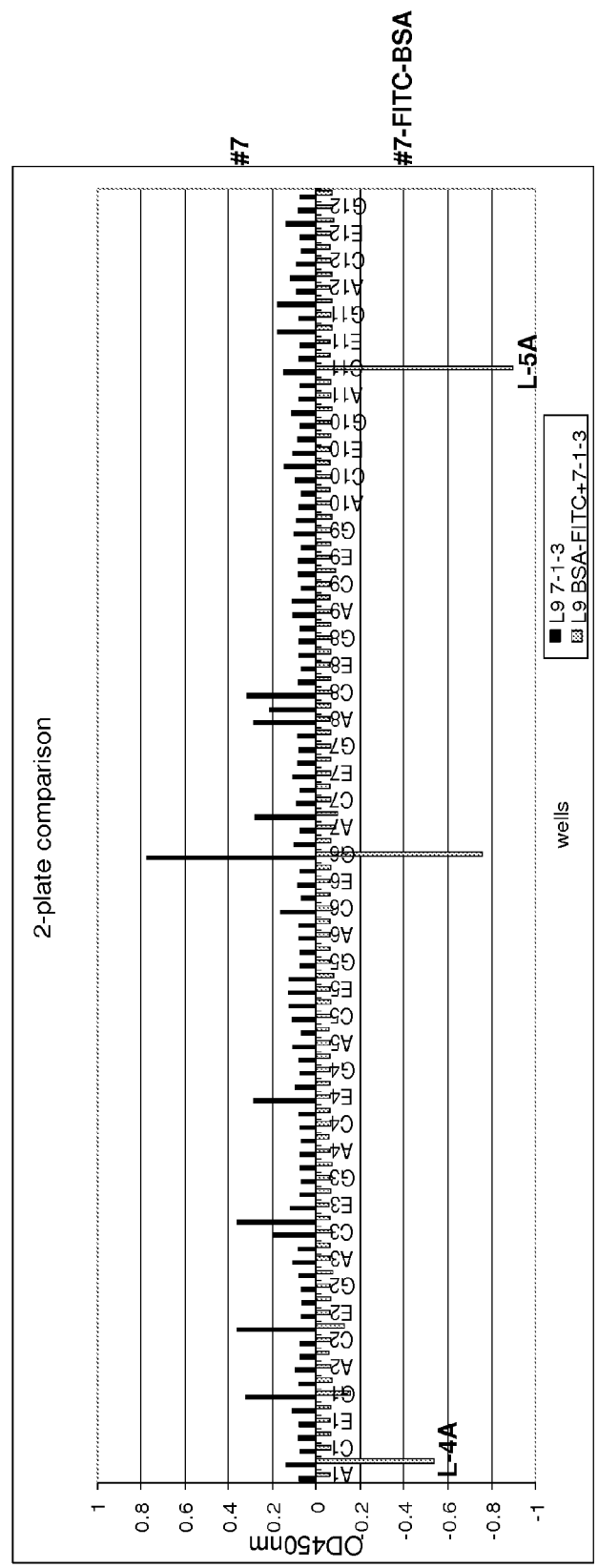
FIG. 5 shows the results obtained by the assay method for L series antibodies.
Figure 5:
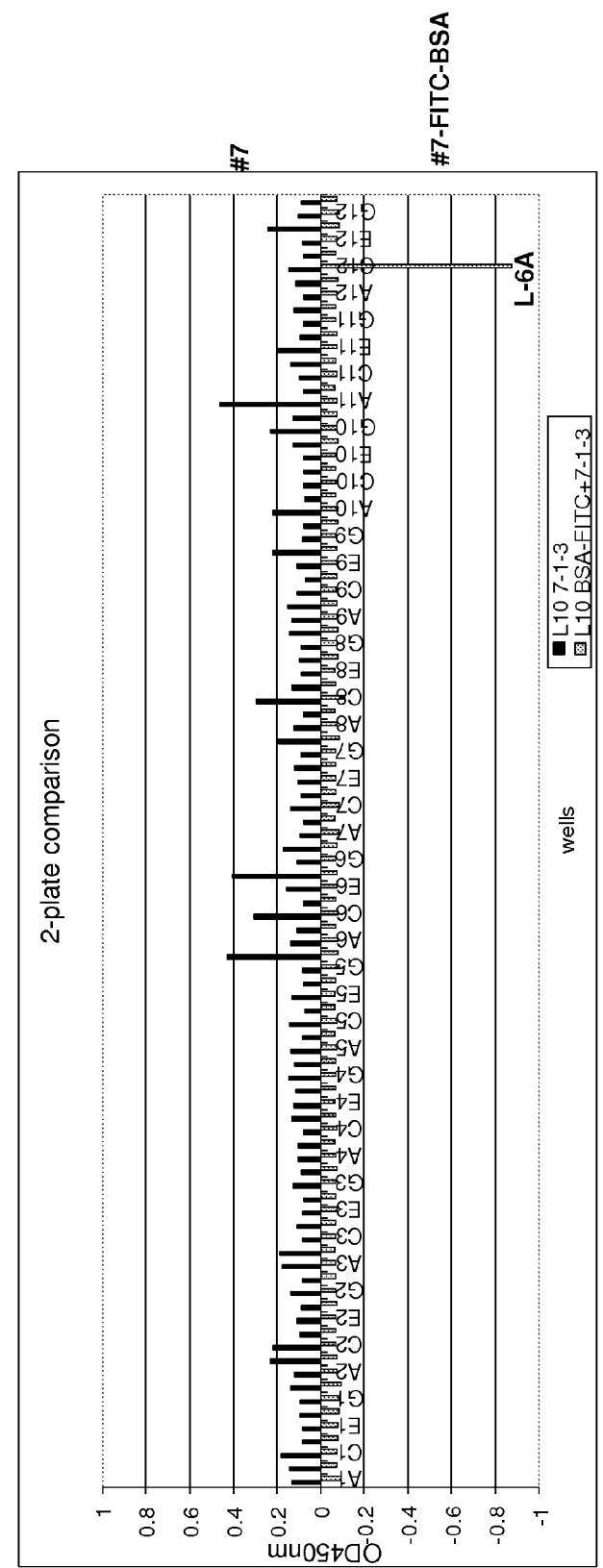
Figure 6:
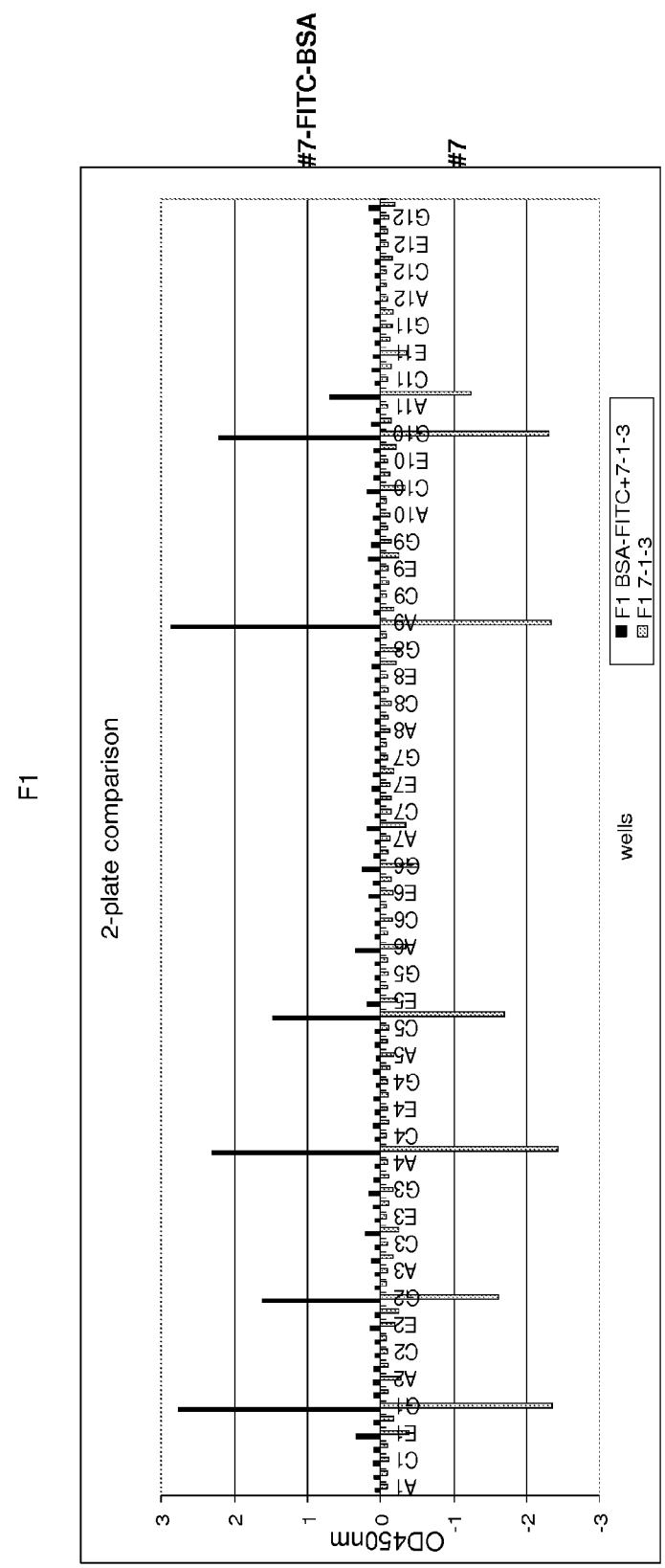
FIG. 6 shows the results obtained by the assay method for F series antibodies.
Figure 6:
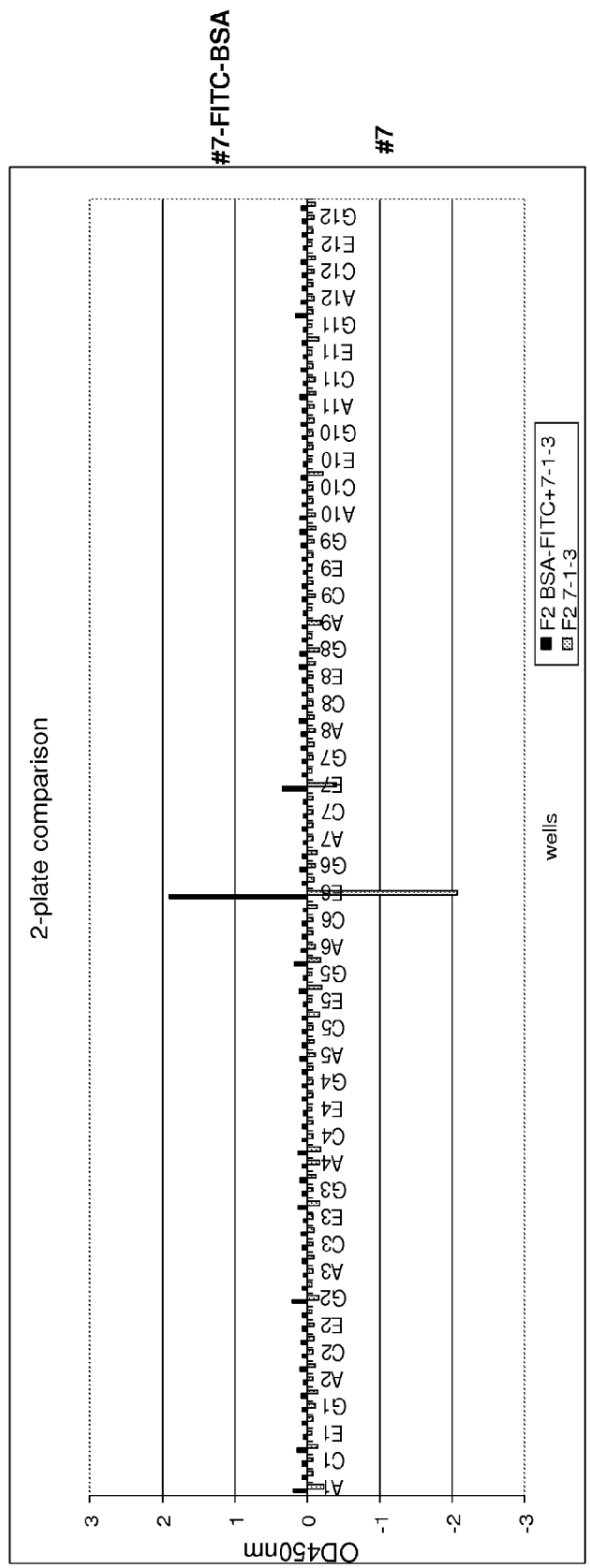
Figure 7:
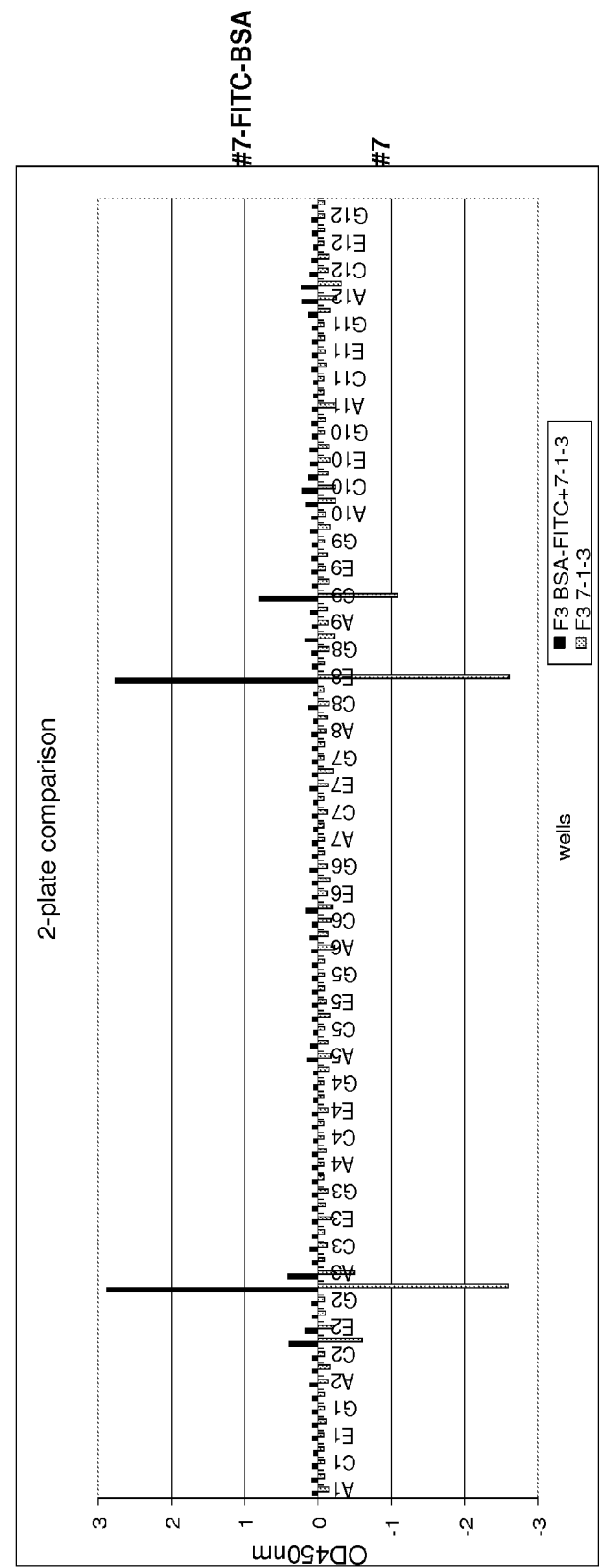
FIG. 7 shows the results obtained by the assay method for F series antibodies.
Figure 8:
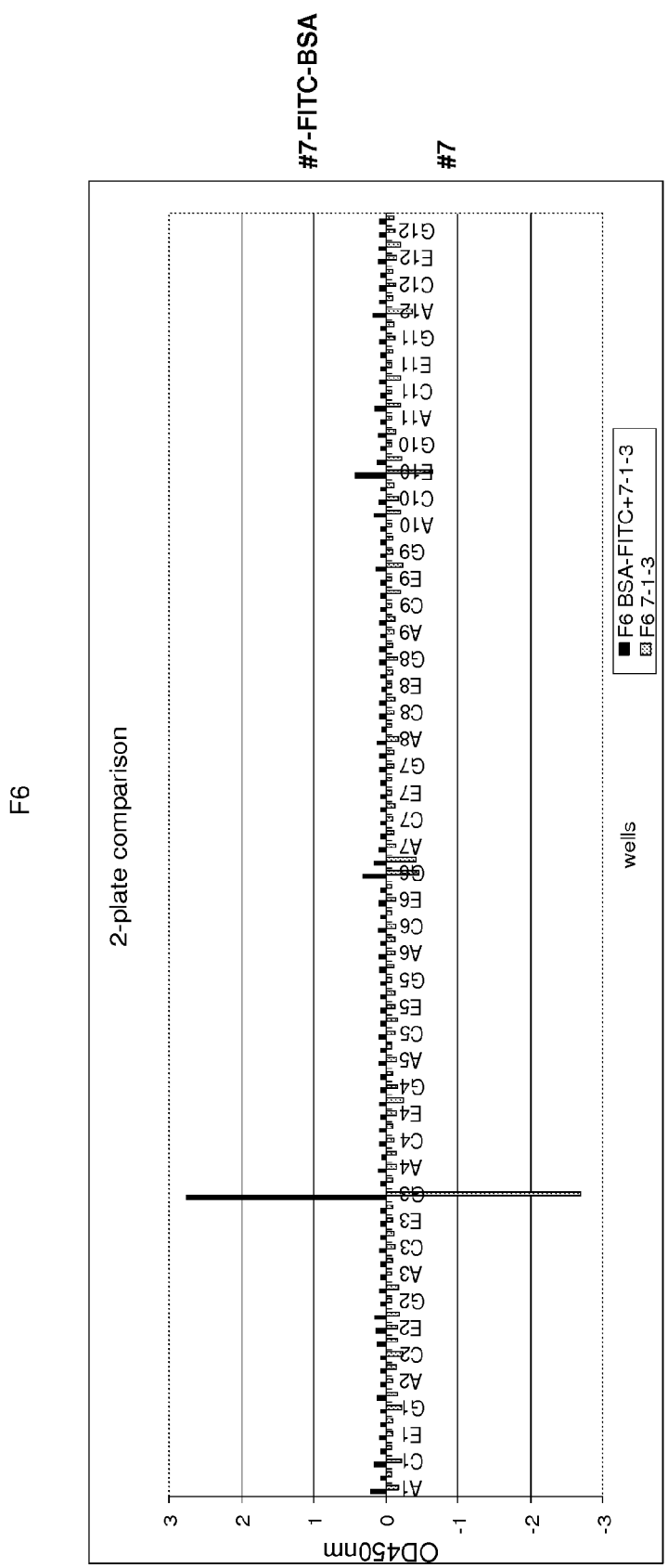
FIG. 8 shows the results obtained by the assay method for F series antibodies.
Figure 9:
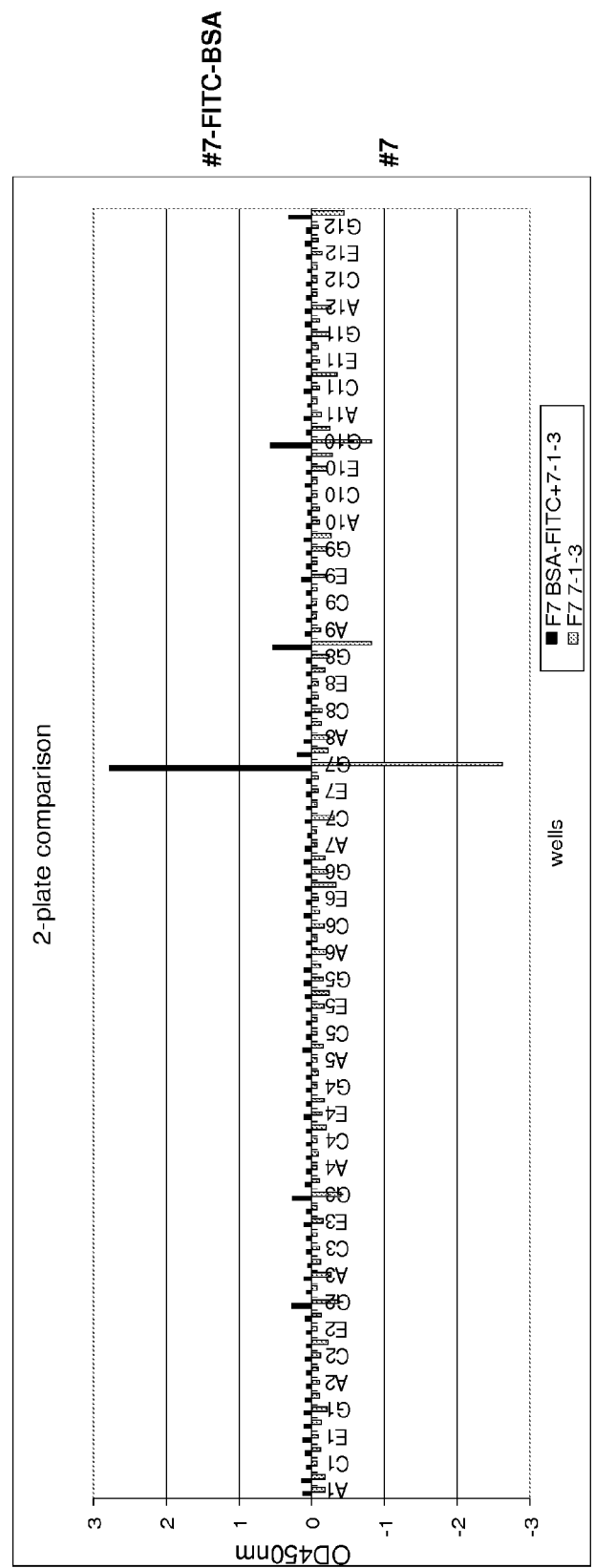
FIG. 9 shows the results obtained by the assay method for F series antibodies.
Figure 9:
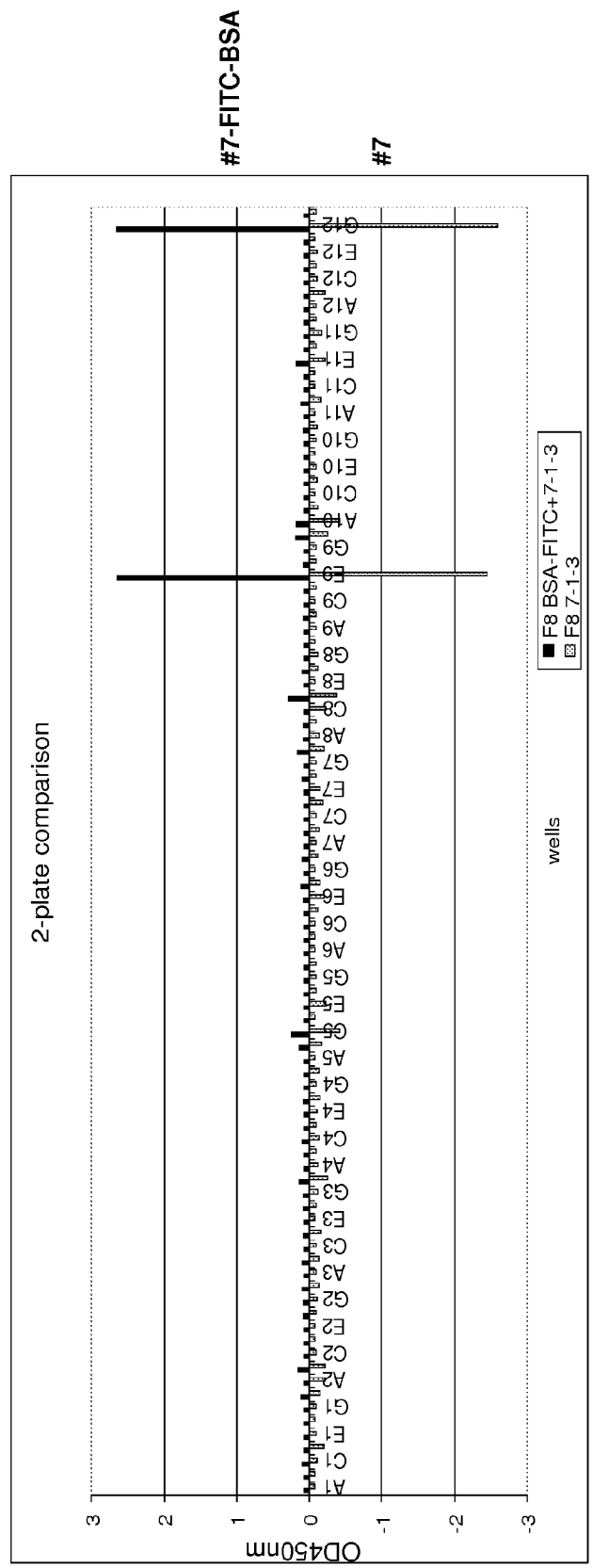
Figure 10:
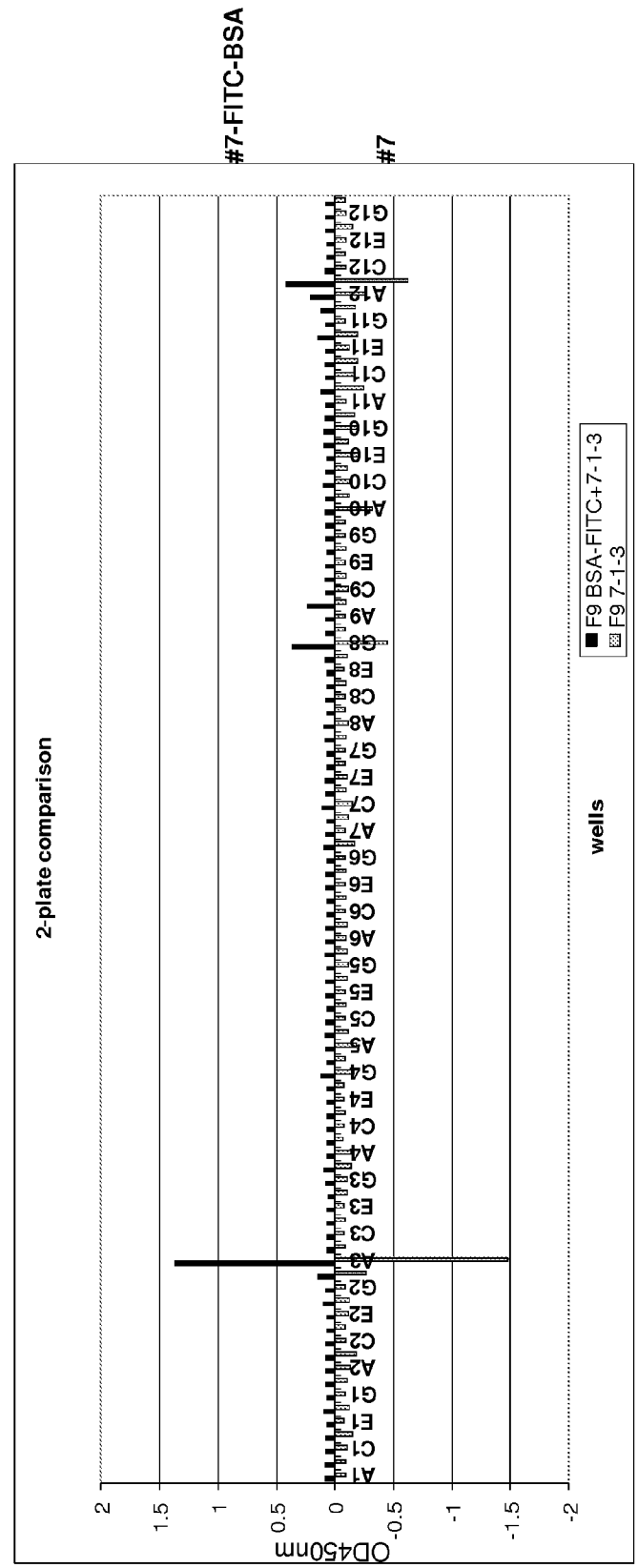
FIG. 10 shows the results obtained by the assay method for F series antibodies.
Figure 10:
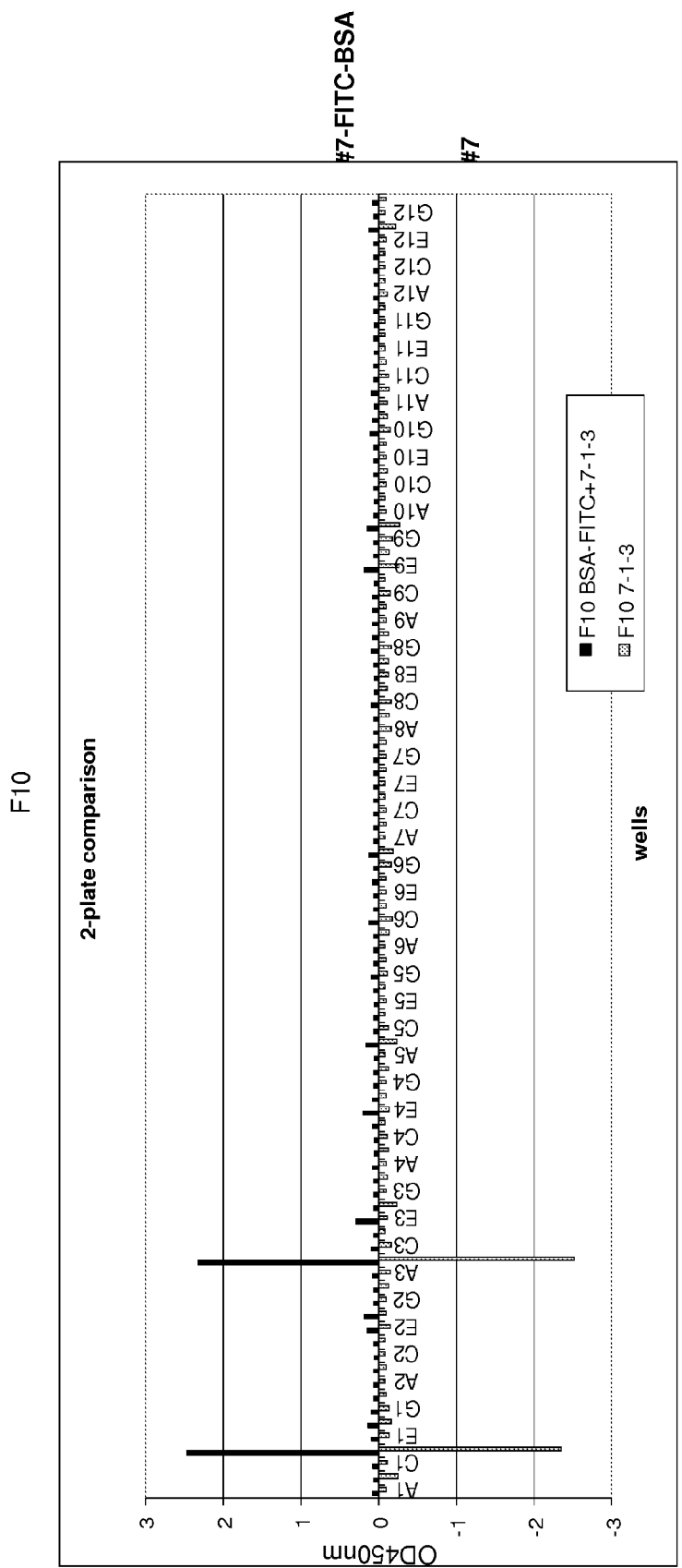

FIGS. 1 to 10 show the results obtained by the assay method for the above antibodies.

In the figures, the target antibody-producing wells are indicated by the numbers in combination with A (domino antibody) or S (antibody-unlocking antibody). Clones showing reactivities of six types of domino antibodies (L-1A to 6A) and three types of antibody-unlocking antibodies (L-1S to 3S) were obtained from the L series, and clones showing a reactivity of one kind of domino antibody (F-1A) were obtained from the F series.

The domino antibody (F-1A, L-6A) producing hybridomas obtained by cloning the hybridoma that produced the target antibodies were deposited with the ATCC on Apr. 23, 2008, and the following ATCC numbers were assigned.
(1) Identification Reference by Depositor: Hybridoma Cell Line F-1A
ATCC Patent Deposit Designation: PTA-9167
(2) Identification Reference by Depositor: Hybridoma Cell Line L-6A
ATCC Patent Deposit Designation: PTA-9168

Example 2

Preparation and Analysis of Anti-λ1 Light Chain Monoclonal Antibody

For the purpose of developing a molecule capable of detecting antigen-antibody reactions, a preparation of monoclonal antibodies (mAb) that recognize conformational changes in an antibody was attempted. As a strategy, mAb having specificity against NP ((4-hydroxy-3-nitrophenyl)acetyl), i.e., hapten, was selected as a model antibody. This attempt was based on the assumption that an mAb clone that binds to a λ1 light chain as an epitope and is capable of detecting antigen-antibody reactions can be isolated by administering anti-NP mAb having λ1 light chain to an SJL mouse for immunization, in which the mouse λ1 light chain is hardly detected in the serum due to mutation of one base present in the λ1 light chain constant region. E11 (IgG2a/λ1) with high affinity, which was used as anti-NP mAb, was mixed with NP14-CGG at a molar ratio of 3:1, and the immunization was performed in a state where antibody-antigen complexes were formed. FIG. 11 shows a detailed immunization schedule. After immunization four times every two weeks, the spleen was extracted and fused with myeloma cell line SP2/0 to produce hybridomas. Screening of the hybridoma secreting useful mAb was carried out by ELISA using the culture supernatant, based on the binding affinity to E11 as the index.

Among the obtained clones, clone #0806-12 having greater antibody production was cultured on a large scale, and subjected to affinity purification using a column in which E11 was covalently bonded to agarose beads. For the confirmation of the epitope for mAb #0806-12, yeast lines that express each Ig domain (VH, CH1, CH2, CH3, VL, and CL domains) of E11 on their surface were produced. The yeast surface was stained using the biotinylated #0806-12 and Streptavidin-PE. As a result of FACS analysis, the #0806-12 only bound to the CL domain-expressing yeast line. This result indicates that Ab #0806-12 binds to the λ1 light chain constant region as the epitope (FIG. 12).

The antibody-unlocking antibody (0806-12) producing hybridoma obtained by cloning the hybridoma that produced the target antibody was deposited with the ATCC on Apr. 16, 2009, and the following ATCC numbers were assigned.

Identification Reference by Depositor: Hybridoma Cell Line 0806-12
ATCC Patent Deposit Designation: PTA-9967

Whether mAb #0806-12 can detect antigen-antibody reactions was analyzed using a Biacore. The purified mAb #0806-12 was immobilized on a Biacore CM5 sensor chip at about 2000 RU by an amine coupling method to examine binding to 9T13 (IgG1/λ1), which is anti-NP mAb (FIG. 13). At this time, analyzing samples previously mixed with NP-Cap (1 µM), which is an antigen, or with DNP-Cap (1 µM, 2,4-dinitrophenyl), which is not an antigen but has a structure similar to NP-Cap, a remarkable decrease in RU value was observed only in the sample (9T13+NP-Cap) that induced antigen-antibody reactions (the RU value was decreased to about ⅙ within 180 seconds after sample injection).

These results show that the anti-λ1 light chain monoclonal antibody #0806-12 thus obtained can detect antigen-antibody reactions, since it specifically binds to anti-NP mAb having λ1 light chain, and the affinity is remarkably decreased upon binding of the anti-NP mAb to the NP antigen.

INDUSTRIAL APPLICABILITY

A. Practical Applications of Antibody that Recognizes Antigen-Recognizing Antibody
1) As Means of Measuring Method
(i) Biosensor: Detection of Small Amount of Antigens (Realization of Supersensitivity)

For example, there is a rat monoclonal antibody (A) that only recognizes an antigen-binding mouse antibody, and hamster monoclonal antibody (B), which responds only when the rat antibody recognizes an antigen. Biosensors can be assembled so as to develop such a chain reaction by changing the recognition site (Fc portion and light chains) or types of antibodies. This suggests that a very small signal can be greatly amplified, providing a highly sensitive sensor.

(ii) As ELISA that does not Require Washing

For example, a primary antibody capable of recognizing an antigen is labeled with fluorescence protein CFP, and for example, the present antibody is labeled with another fluorescence protein YFP. When a fixed amount of primary antibody and present antibody are added to a solution containing the antigen, fluorescence resonance energy transfer (FRET) is observed depending on the amount of the antigen.

This measuring method does not require purification and labeling of the antigen, and is applicable to any measurement when there is a primary antibody that responds to the antigen.

2) As Drugs (i) Universal Enhancer Antibody for an Antibody Drug

The present antibody can enhance ADCC and CDCC reactions initiated when an antibody drug, which has already been approved and utilized as a drug, binds to an antigen in the body. For example, an antibody drug that recognizes a cancer antigen is administered to a patient, and a part of the administered antibody arrives at a focus site. At this time, the present antibody, when administered, reacts with and binds to the antibody drug bound to the antigen in the focus site.

The present antibody also can label an anticancer drug and radioactivity, allowing its use as an enhancer for a wide variety of antibody drugs. The present antibody can be used as an enhancer for any kind of antibody drugs as long as they contain human antibodies to which the present antibody can respond. In addition, it is safe to accidentally administer an excessive amount of the present antibody since it responds only to a drug antibody bound to an antigen.

(ii) Enhancer for Natural Antibody Obtained During Infectious Disease Outbreaks and During Tumor-Bearing During the invasion of foreign substances (virus and bacteria), or during the development or progression of tumors, the body has a considerable reaction, promoting the removal of the foreign substances and the inhibition of tumor growth. That is, antibodies are presumably produced against the foreign substances or tumor upon such a response, although the amount of such antibodies may not be sufficient. Accordingly, the antibodies capturing foreign substances or tumor cells can be enhanced by administering the present antibody to support reactions of the body. Thus, in this case, the present antibody can be used as more effective globulin preparations to enhance the natural immunity of the body, while in Section (i), the present antibody is used to enhance the administered antibody drug.

3) As Medical Equipment (i) Column for Removing Antigen-Antibody Complex

The present antibody can be immobilized on a column for use. For some diseases, a large amount of immune complex is known to contribute to the disease progression (e.g., chronic rheumatoid arthritis, SLE, etc.). A column immobilized with the present antibody can be used as an extracorporeal-circulation column to circulate the blood of a patient, removing immune complex antibodies bound to the antigen. Other antibodies that are not involved in the immune complexes are not absorbed to the column and return to the body. Thus, the column is characterized by removing only the immune complex that causes the progression of the disease.

(ii) Column for Removing Small Amount of Toxic Substance

In the same manner as in Section (i), the present antibody can be used to remove a toxic substance that is accidentally introduced into the body. In this case, an antibody capable of binding to the toxic substance is prepared. The present antibody, which reacts with the above antibody when it binds to the toxic substance, is bound to the column. For the purpose of removing the toxic substance, the primary antibody capable of binding to the toxic substance is injected intravenously into the body in which the toxic substance has been taken. Immediately, the column efficiently removes only the antibody bound to the toxic substance starting to circulate around the body.

Further, taking advantage of tasteless, odorless and easy water solubility of antibodies, a toxic substance mixed in tap water, drinking water, or the like can be removed by adding dropwise a primary antibody capable of binding to the toxic substance to the drinking water, and then passing the water through a filter immobilized with the present antibody. Detoxification of such poisoned water is thus possible.

Similarly, the present antibody is also applicable to the removal of toxic substances in the air.

B. As practical applications of the antibody (antibody-unlocking antibody) that recognizes an antibody that does not recognize an antigen, the present antibody with high affinity is supposed to function to dissociate an antigen from an antibody that recognizes the antigen.

1) As Drugs (i) As Anti-Allergic Drugs

Since the present antibody strongly reacts with IgE unbound to an antigen, even when IgE is bound to an allergen, i.e., an antigen, the antigen is dissociated from the IgE antibody by the binding of the present antibody to the IgE. Thus, IgE bound to an allergen (antigen) can be prevented from inducing allergic reactions.

(ii) As Emergency Antibody for Coping with Shocks Common to Antibody Drugs

From a standpoint similar to the above, it is necessary in some cases to relieve the binding of antibodies to cope with shocks caused by antibody administration. Some antibodies, which will be developed and tested in clinical trials from now on, could possibly result in an incident such as, for example, TeGenero's clinical trial of administration of agonistic antibodies in Britain. The present antibody presumably releases the bond of an administered antibody to an antigen, contributing to withdrawal from shock symptoms.

(iii) Therapeutic Agents for Diseases Induced by Appearance of Specific Antibody This adaptation is basically the same as the above two applications. For example, the present antibody is injected into the body and dissociates in vivo the antigen and the antibody of the antigen-antibody complex that is removed under extracorporeal circulation in Section A. 3) (i).

The invention claimed is:

1. An isolated antibody, wherein the isolated antibody specifically recognizes a first antibody bound to fluorescein isothiocyanate (FITC).

2. A hybridoma deposited under ATCC accession number PTA-9167 or PTA-9168.

3. A method for obtaining a domino antibody, comprising:
combining a first antibody with a hapten or antigen,
chemically fixing or bonding the hapten or antigen to the antibody to prepare an antigen-antibody complex in which the hapten or antigen does not dissociate from the antibody, and
immunizing a host with the complex,
obtaining at least one hybridoma from the spleen cells of the host, wherein the hybridoma produces monoclonal antibodies, and obtaining a domino antibody from the monoclonal antibodies produced by the obtained hybridoma, wherein the domino antibody specifically recognizes conformational changes in the first antibody when the first antibody is bound to the hapten or antigen.

4. The method of claim 3, wherein the antigen comprises at least one of gamma globulin, bovine serum albumin, fluorescein isothiocyanate (FITC), and (4-hydroxy-3-nitrophenyl)acetyl (NP).

5. The method of claim 3, wherein the host is a mouse, a rat, a rabbit, a hamster, or a monkey.

* * * * *